(12) United States Patent
Yen et al.

(10) Patent No.: US 10,624,897 B2
(45) Date of Patent: Apr. 21, 2020

(54) CHLOROBENZENE SUBSTITUTED AZAARYL COMPOUNDS

(71) Applicant: TAIPEI MEDICAL UNIVERSITY, Taipei (TW)

(72) Inventors: Yun Yen, Arcadia, CA (US); Jing-Ping Liou, Taipei (TW); Chun-Han Chen, Taipei (TW)

(73) Assignee: Taipei Medical University, Taipei (TW)

( * ) Notice: Subject to any disclaimer, the term of this patent is extended or adjusted under 35 U.S.C. 154(b) by 0 days.

(21) Appl. No.: 15/746,182

(22) PCT Filed: Jul. 20, 2016

(86) PCT No.: PCT/US2016/043203
§ 371 (c)(1),
(2) Date: Jan. 19, 2018

(87) PCT Pub. No.: WO2017/015400
PCT Pub. Date: Jan. 26, 2017

(65) Prior Publication Data
US 2019/0083499 A1    Mar. 21, 2019

Related U.S. Application Data

(60) Provisional application No. 62/194,705, filed on Jul. 20, 2015.

(51) Int. Cl.
| | |
|---|---|
| *A61K 31/53* | (2006.01) |
| *A61K 45/06* | (2006.01) |
| *A61K 31/7068* | (2006.01) |
| *A61K 31/5377* | (2006.01) |
| *C07D 239/48* | (2006.01) |
| *C07D 401/02* | (2006.01) |
| *C07D 239/42* | (2006.01) |
| *C07D 405/02* | (2006.01) |
| *A61P 35/00* | (2006.01) |

(52) U.S. Cl.
CPC .......... *A61K 31/53* (2013.01); *A61K 31/5377* (2013.01); *A61K 31/7068* (2013.01); *A61K 45/06* (2013.01); *A61P 35/00* (2018.01); *C07D 239/42* (2013.01); *C07D 239/48* (2013.01); *C07D 401/02* (2013.01); *C07D 405/02* (2013.01)

(58) Field of Classification Search
CPC .............. A61K 31/53; A61K 31/5377; A61K 31/7068; A61K 45/06; C07D 401/02; C07D 405/02; C07D 239/42

USPC .................................................... 544/8
See application file for complete search history.

(56) References Cited

U.S. PATENT DOCUMENTS

| 8,759,517 B2 | 6/2014 | Bold et al. |
| 2009/0137804 A1 | 5/2009 | Ding et al. |

FOREIGN PATENT DOCUMENTS

| CN | 101035769 A | 9/2007 |
| WO | WO 2013-144339 A1 | 10/2013 |
| WO | 2015057938 A1 | 4/2015 |

OTHER PUBLICATIONS

Chell, V. et al., Tumour Cell Responses to New Fibroblast Growth Factor Receptor Tyrosine Kinase Inhibitors and Identification of a Gatekeeper Mutation in FGFR3 as a Mechanism of Acquired Resistance, Oncogene. Jun. 20, 2013;32(25):3059-70.
Chou, Ting-Chao et al., Theoretical Basis, Experimental Design, and Computerized Simulation of Synergism and Antagonism in Drug Combination Studies, Pharmacol Rev. Sep. 2006;58(3):621-81.
Helsten, Teresa et al., The FGFR Landscape in Cancer: Analysis of 4,853 Tumors by Next-Generation Sequencing, Clin Cancer Res. Jan. 1, 2016;22(1):259-67.
Ronchetti, Domenica et al., Deregulated FGFR3Mutants in Multiple Myeloma Cell Lines with t(4;14): Comparative Analysis of Y373C, K650E and the Novel G384D Mutations, Oncogene. Jun. 14, 2001;20(27):3553-62.
Zhang, Yan et al., Constitutive Activating Mutation of the FGFR3b in Oral Squamous Cell Carcinomas, Int. J. Cancer, Oct. 20; 117(1): 166-8.
Office Action in Taiwan Counterpart Application No. 105122966, dated Oct. 7, 2019, in 4 pages; English translation provided.
Das, Gautam, et al. "Regulation and function of autophagy during cell survival and cell death." Cold Spring Harbor Perspectives in Biology 4.6 (2012): a008813, Cold Spring Harbor Laboratory Press, 12 pages.
Extended European Search Report in EP Application No. 16828495. 8, dated Jan. 31, 2019, in 7 pages.
International Search Report in International Patent Application No. PCT/US16/43203, dated Sep. 28, 2016, in 2 pages.
Chun-Han Chen et al: "Trichlorobenzene-substituted azaaryl compounds as novel FGFR inhibitors exhibiting potent antitumor activity in bladder cancer cells in vitro and in vivo", Oncotarget, vol . 7, No. 18, May 3, 2016 (May 3, 2016), 14 pages; XP055544468, D0I : 10.18632/oncotarget.8380.

*Primary Examiner* — Kahsay Habte
(74) *Attorney, Agent, or Firm* — Duane Morris LLP

(57) ABSTRACT

The invention provides a series of chlorobenzene substituted azaaryl compounds having activity in inhibiting cancer cell growth and low toxicity to normal cells. Particularly, the compounds of the invention have stronger inhibition effect on bladder cancer and liver cancer.

17 Claims, 10 Drawing Sheets

A

CHLOROBENZENE SUBSTITUTED AZAARYL COMPOUNDS

CHLOROBENZENE SUBSTITUTED AZAARYL COMPOUNDS

This application claims the benefit of priority of, and is U.S. 371 National Phase Application of International Patent Application No. PCT/US2016/043203, filed Jul. 20, 2016, which claims priority to U.S. Provisional Application No. 62/194,705, filed Jul. 20, 2015, the contents of each of which are hereby incorporated by reference in their entirety.

FIELD OF THE INVENTION

The invention relates to a series of anti-cancer compounds and the pharmaceutical preparations thereof as well as their methods of use. Particularly, the invention provides chlorobenzene substituted azaaryl compounds having anti-cancer activity.

BACKGROUND OF THE INVENTION

Cancer, a disease in which cells in a part of the body experience out-of-control growth, is one of the most life threatening diseases. This disease is currently treated principally by surgical therapy in combination with radiation therapy and/or chemotherapy. In spite of recent development of novel surgical techniques and discovery of novel anti-cancer agents, the existing treatment of cancer has an insufficiently improved outcome, except for some cancer types. In particular, no drugs for targeted therapy have been developed for treating bladder cancers, and the drug sorafenib, targeted against liver cancer, cannot provide a good therapeutic efficacy for most patients. U.S. Pat. No. 8,759,517 B2 provides pyrimidinyl aryl urea derivatives useful in the treatment, of protein kinase dependent diseases. WO 2013144339 relates to 3-(2,6-Dichloro-3,5-dimethoxy-phenyl)-1-{6-[4-(4-ethyl-piperazin-1-yl)-phenylamino]-pyrimid-4-yl}-1-methyl-urea or a pharmaceutically acceptable salt or solvate thereof or a pharmaceutical composition comprising the same for use in the treatment of fibroblast growth factor receptor mediated disorders.

However, there is a continued need to provide compounds for use as therapeutics for treating cancers and other diseases.

SUMMARY OF THE INVENTION

One aspect of the invention is to provide a compound having the following Formula (I):

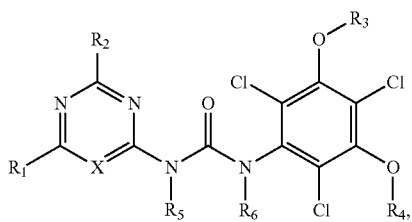

(I)

or a tautomer, stereoisomer or enantiomer thereof, or a solvate, prodrug or pharmaceutically acceptable salt thereof.

Another aspect of the invention is to provide a pharmaceutical composition containing a compound of Formula (I).

A further aspect is to provide a method for inhibiting, preventing or treating a cancer, comprising administrating a compound of Formula (I) to a cell or a subject in need thereof.

DETAILED DESCRIPTION OF THE INVENTION

Figure 1:
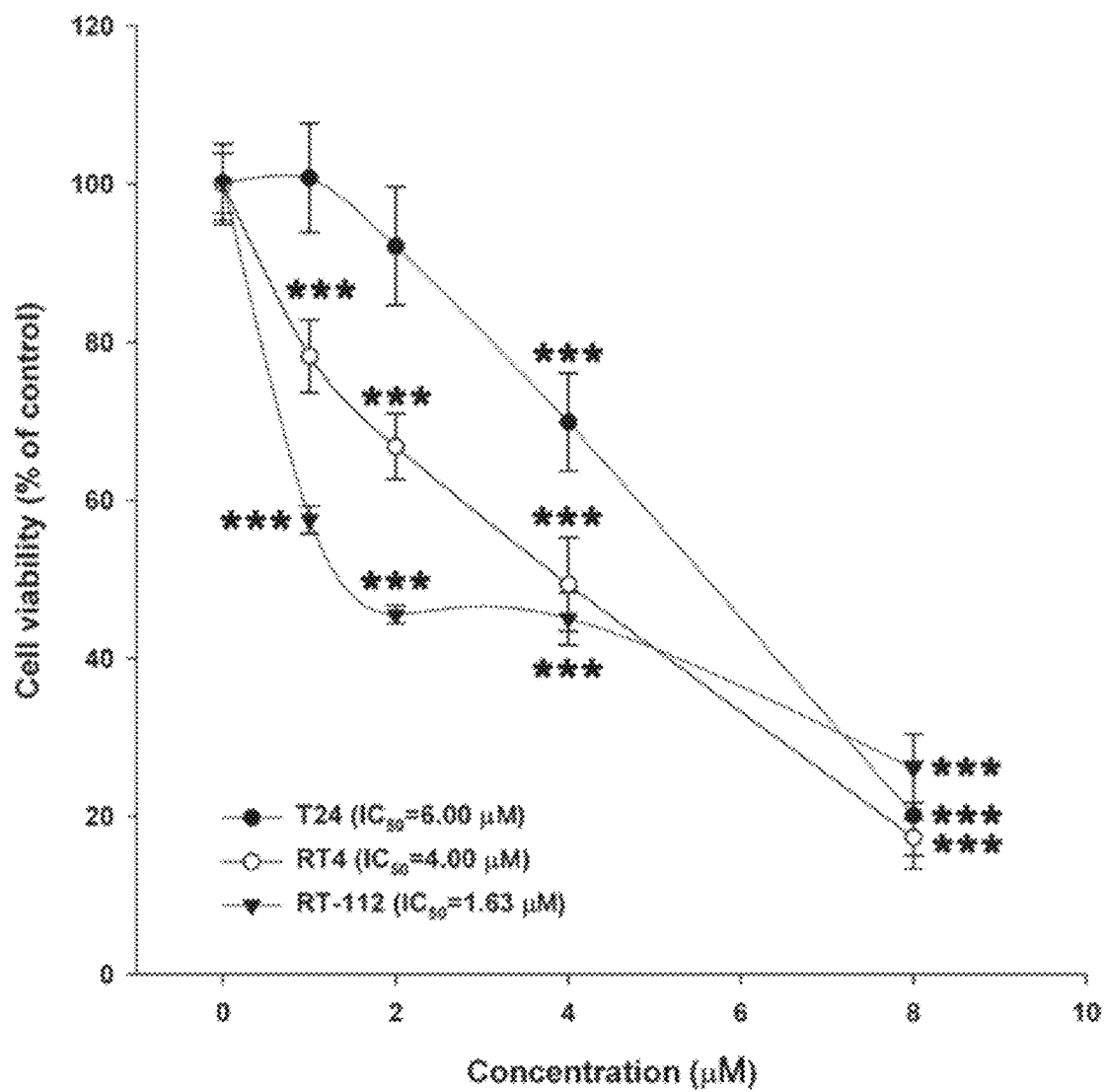
FIGS. 1A and 1B show that MPT0L145 inhibits FGFR signaling and exerts anti-growth effects on FGFR-activated cancer cell lines. A. Effects of MPT0L145 on the viability of bladder cancer cells. RT-112, RT4 and T24 cells were treated with the indicated concentrations of MPT0L145 for 72 h. Cell viability was assessed the MTT assay. Data are expressed as means±S.D. (*P<0.001 comparing to control group) B. MPT0L145 has less toxicity relative to normal cells. HUVECs were treated with indicated concentrations of MPT0L145 for 72 hours and viability was examined by MTT assay. Data are expressed as means±S.D. (*P<0.001 compares to control group).
Figure 1:
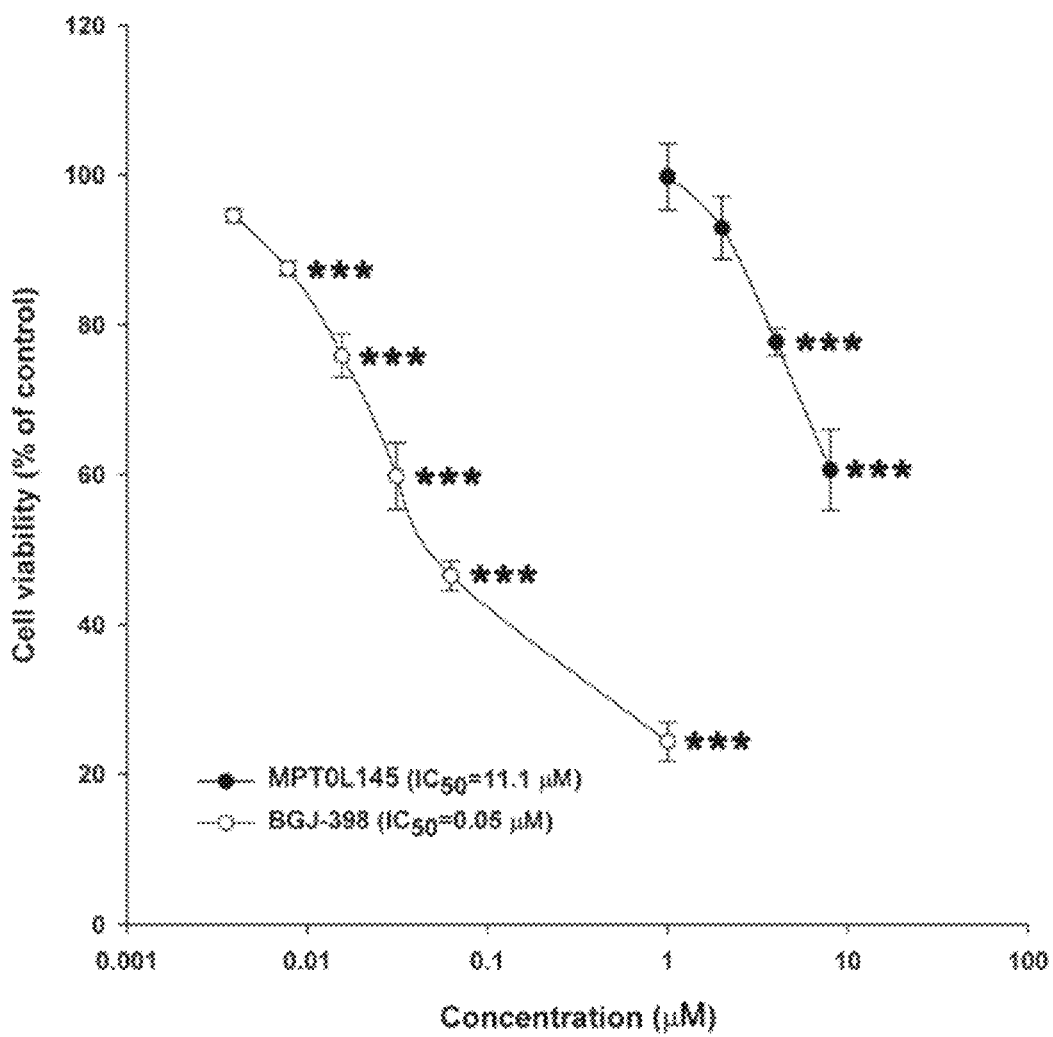

The invention provides a series of chlorobenzene substituted azaaryl compounds having activity in inhibiting cancer cell growth and low toxicity to normal cells. Particularly, the compounds of the invention have stronger inhibition effect on bladder cancer and liver cancer.

Terms not specifically defined herein should be understood according to the meaning that would be given to them by one of skill in the art in light of the disclosure and the context. As used in the specification, however, unless specified to the contrary, the following terms have the meaning indicated and the following conventions are adhered to.

The terms "a" and "an" refer to one or more.

The terms "disease" and "disorder" herein can be used interchangeably.

The terms "treatment" and "treating" embrace both preventative, i.e. prophylactic, or therapeutic, i.e. curative and/or palliative, treatment. Thus the terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compounds, compositions and methods of the present invention may be used for instance as therapeutic treatment over a period of time as well as for chronic therapy. In addition the terms "treatment" and "treating" comprise prophylactic treatment, i.e. treatment of patients at risk of developing a condition mentioned hereinbefore, thus reducing said risk.

The term "therapeutically effective amount" means an amount of a compound of the present invention that (i) treats or prevents the particular disease or condition, (ii) attenuates, ameliorates, or eliminates one or more symptoms of the particular disease or condition, or (iii) prevents or delays the onset of one or more symptoms of the particular disease or condition described herein.

The term "substituted" as used herein, means that any one or more hydrogens on the designated atom, radical or moiety are replaced with a selection from the indicated group, provided that the atom's normal valence is not exceeded, and that the substitution results in an acceptably stable compound.

The term "pharmaceutically acceptable" is employed herein to refer to those compounds, materials, compositions, and/or dosage forms which are, within the scope of medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines, pyridine, pyrimidine and quinazoline; alkali or organic salts of acidic residues such as carboxylic acids; and the like.

As used herein, the term "stereoisomer" is a general term for all isomers of individual molecules that differ only in the orientation of their atoms in space. It includes enantiomers and isomers of compounds with more than one chiral center that are not mirror images of one another (diastereoisomers).

The term "chiral center" refers to a carbon atom to which four different groups are attached.

The terms "enantiomer" and "enantiomeric" refer to a molecule that cannot be superimposed on its mirror image and hence is optically active, wherein the enantiomer rotates the plane of polarized light in one direction and its mirror image compound rotates the plane of polarized light in the opposite direction.

The term "racemic" refers to a mixture of equal parts of enantiomers which is optically inactive.

The term "resolution" refers to the separation or concentration or depletion of one of the two enantiomeric forms of a molecule.

As used herein, halo or halogen refers to fluoro, chloro, bromo or iodo.

As used herein, the term "alkyl" refers to straight or branched hydrocarbon chains containing the specified number of carbon atoms. For example, "$C_1$-$C_6$ alkyl" is selected from straight-chained and branched non-cyclic hydrocarbons having from 1 to 6 carbon atoms. Representative straight chain $C_1$-$C_6$ alkyl groups include -methyl, -ethyl, -n-propyl, -n-butyl, -n-pentyl, and -n-hexyl. Representative branched $C_1$-$C_6$ alkyls include -isopropyl, -sec-butyl, -isobutyl, -tert-butyl, -isopentyl, -neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, and 3,3-dimethylbutyl.

As used herein, the term "alkenyl" refers to straight or branched chain hydrocarbon chains containing the specified number of carbon atoms and one or more double bonds. For example, "$C_2$-$C_6$ alkenyl" is selected from straight chain and branched non-cyclic hydrocarbons having from 2 to 6 carbon atoms and including at least one carbon-carbon double bond. Representative straight chain and branched $C_2$-$C_6$ alkenyl groups include -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexenyl, 2-hexenyl, and 3-hexenyl.

As used herein, a "$C_2$-$C_6$ alkynyl" is selected from straight chain and branched non-cyclic hydrocarbon having from 2 to 6 carbon atoms and including at least one carbon-carbon triple bond. Representative straight chain and branched $C_2$-$C_6$ alkynyl groups include -acetylenyl, -propynyl, -1-butyryl, -2-butyryl, -1-pentynyl, -2-pentynyl, -3-methyl-1-butynyl, -4-pentynyl, -1-hexynyl, -2-hexynyl, and -5-hexynyl.

As used herein, "cycloalkyl" refers to a group selected from $C_3$-$C_{12}$ cycloalkyl, and preferably a $C_{3-8}$ cycloalkyl. Typical cycloalkyl groups include cyclopropyl, cyclobutyl, cyclopentyl, cyclohexyl, cycloheptyl, cyclooctyl, and cyclononyl.

As used herein, the term "alkoxy" refers to a straight or branched alkoxy group containing the specified number of carbon atoms. For example, $C_{1-6}$alkoxy means a straight or branched alkoxy group containing at least 1, and at most 6, carbon atoms. Examples of "alkoxy" as used herein include, but are not limited to, methoxy, ethoxy, propoxy, prop-2-oxy, butoxy, but-2-oxy, 2-methylprop-1-oxy, 2-methylprop-2-oxy, pentoxy and hexyloxy. The point of attachment may be on the oxygen or carbon atom.

As used herein, the term "alkylthio (also termed alkylsulfanyl) refers to straight-chain or branched alkyl groups (preferably having 1 to 6 carbon atoms, e.g. 1 to 4 carbon atoms ($C_1$-$C_6$-alkylthio), which are bound to the remainder of the molecule via a sulfur atom at any bond in the alkyl group. Examples of $C_1$-$C_4$-alkylthio include methylthio, ethylthio, n-propylthio, isopropylthio, n-butylthio, sec-butylthio, isobutylthio and tert-butylthio. Examples of $C_1$-$C_6$-alkylthio include, apart from those mentioned for $C_1$-$C_4$-alkylthio, 1-, 2- and 3-pentylthio, 1-, 2- and 3-hexylthio and the positional isomers thereof."

As used herein, the term "alkoxyalkyl" refers to the group -$alk_1$-O-$alk_2$ where $alk_1$ is alkyl or alkenyl, and $alk_2$ is alkyl or alkenyl.

As used herein, the term "alkylamino" refers to the group —NRR' where R is alkyl and R' is hydrogen or alkyl.

As used herein, "aryl" refers to a group selected from $C_{6-14}$ aryl, especially $C_{6-10}$ aryl. Typical $C_{6-14}$ aryl groups include phenyl, naphthyl, phenanthryl, anthracyl, indenyl, azulenyl, biphenyl, biphenylenyl and fluorenyl groups.

As used herein, "heteroaryl" refers to a group having from 5 to 14 ring atoms; 6, 10 or 14 pi electrons shared in a cyclic array; and containing carbon atoms and 1, 2 or 3 oxygen, nitrogen and/or sulfur heteroatoms. Examples of heteroaryl groups include indazolyl, furyl, thienyl, pyrrolyl, imidazolyl, oxazolyl, thiazolyl, imidazolyl, pyrazolyl, isoxazolyl, isothiazolyl, oxadiazolyl, triazolyl, thiadiazolyl, pyridyl, pyridazinyl, pyrimidinyl, pyrazinyl, tetrazolyl, triazinyl, azepinyl, oxazepinyl, morpholinyl, thiazepinyl, diazepinyl, thiazolinyl, benzimidazolyl, benzoxazolyl, imidazopyridinyl, benzoxazinyl, benzothiazinyl, benzothiophenyl oxazolopyridinyl, benzofuranyl, quinolinyl, quinazolinyl, quinoxalinyl, benzothiazolyl, phthalimido, benzofuranyl, benzodiazepinyl, indolyl, indanyl, azaindazolyl, deazapurinyl and isoindolyl.

As used herein, the term "therapeutically effective amount" is meant to refer to an amount of an active agent or combination of agents effective to ameliorate or prevent the symptoms. Determination of a therapeutically effective amount is well within the capabilities of those skilled in the art, especially in light of the detailed disclosure provided herein.

In one aspect, the invention provides a compounds having the following Formula (I):

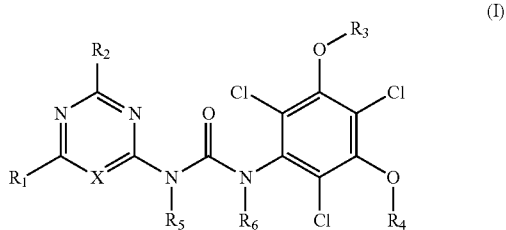

wherein
X is C, N, O or S;
$R_1$ is cycloalkyl; aryl unsubstituted or substituted by halo, carbonyl, hydroxy, amino, nitro, cyano, alkyl, alkenyl, alkynyl, alkoxy, alkylthio, alkoxyalkyl, alkylamino, or heteroaryl having 1 to 3 heteroatoms selected from the group consisting of N, O and S; heteroalkyl unsubstituted or substituted by halo, carbonyl, hydroxy, amino, nitro, cyano, alkoxy, alkylthio, alkoxyalkyl, alkylamino, or heteroaryl having 1 to 3 heteroatoms selected from the group consisting of N, O and S; or $NR_7R_8$ wherein $R_7$ and $R_8$ are each independently selected from the group consisting of H, nitro, amino, cyano, alkyl, alkenyl, alkynyl, aryl or heteroaryl wherein alkyl, alkenyl, alkynyl, aryl and heteroaryl are each independently substituted by heteroaryl having 1 to 3 heteroatoms selected from the group consisting of N, O and S and substituted by alkyl, alkenyl or alkynyl or alkoxy;
$R_2$ is H, halo, carbonyl, hydroxy, amino, nitro, cyano, alkyl, alkenyl, alkynyl or aryl unsubstituted or substituted by halo, hydroxy, amino, nitro, cyano, alkyl, alkenyl or alkynyl; and
$R_3$ and $R_4$ are each independently selected from the group consisting of alkyl, alkenyl, alkynyl, alkoxy, alkylthio, alkoxyalkyl or alkylamino; and
$R_5$ and $R_6$ are each independently selected from H, halo, carbonyl, hydroxy, amino, nitro, cyano, alkyl, alkenyl, alkynyl;
wherein the above-mentioned heteroaryl is unsubstituted or substituted by halo, carbonyl, hydroxy, amino, nitro, cyano, alkyl, alkenyl, alkynyl, alkoxy, alkylthio, alkoxyalkyl, alkylamino or aryl;
or a tautomer or stereoisomer thereof, or a solvate, prodrug or a pharmaceutically acceptable salt thereof.

In some embodiments of formula (I), halo is F, Cl or Br; alkyl is $C_{1-10}$alkyl, preferably $C_{1-6}$alkyl or $C_{1-4}$alkyl; alkenyl is $C_{2-10}$alkenyl, preferably $C_{2-6}$alkenyl; alkynyl is $C_{2-10}$alkynyl, preferably $C_{2-6}$alkynyl; alkoxy is $C_{1-10}$alkoxy, preferably $C_{1-6}$alkoxy or $C_{1-4}$alkoxy; aryl is 5- or 6-membered aryl, preferably phenyl; and heterozryl is 5- or 6-membered heteroaryl and has 1 to 3 heteroatoms selected from the group consisting of N, O and S.

In some embodiments of formula (I), X is C; $R_1$ is phenyl unsubstituted or substituted by halo, cyano, nitro, $C_{1-10}$alkoxy or $C_{5-12}$heteroaryl having 1 to 3 heteroatoms selected from the group consisting of N, O and S and unsubstituted or substituted by $C_{1-10}$alkyl; or unsubstituted or substituted heteroaryl having 1 to 3 heteroatoms selected from the group consisting of N, O and S; $R_2$ is H; $R_3$ and $R_4$ are each independently $C_{1-10}$alkyl; and $R_5$ and $R_6$ are each independently H or $C_{1-10}$alkyl. Preferably, X is C; $R_1$ is phenyl, $C_{1-10}$alkylpiperazinylphenyl, $C_{1-10}$alkyloxyphenyl, halophenyl, cyanophenyl, nitrophenyl, furyl or pyridinyl. More preferably, X is C; $R_1$ is (4-ethylpiperazinyl-1-yl) phenyl, phenyl, 4-methoxyphenyl, 4-fluorophenyl, 4-chlorophenyl, 4-cyanophenyl, nitrophenyl, 2-furyl, 3-pyridinyl or 4-pyridinyl. More preferably, $R_1$ is phenyl, (4-ethylpiperazinyl-1-yl)phenyl, phenyl, 4-methoxyphenyl, 4-fluorophenyl, 4-chlorophenyl, 4-cyanophenyl, nitrophenyl, 2-furyl, 3-pyridinyl or 4-pyridinyl; $R_2$ is H; $R_3$ and $R_4$ are each independently $CH_3$; and $R_5$ and $R_6$ are each independently H or $C_{1-10}$alkyl.

In some other embodiment of formula (I), X is C or N; $R_1$ is $NR_7R_8$ wherein $R_7$ and $R_8$ are each independently selected from the group consisting of H, $C_{1-10}$alkyl substituted by 6-membered heteroaryl unsubstituted or substituted by $C_{1-10}$alkyl; phenyl substituted by 6-membered heteroaryl having 1 to 3 heteroatoms selected from the group consisting of N, O and S and substituted by $C_{1-10}$alkyl; $R_2$ is H, halo or phenyl; $R_3$ and $R_4$ are each independently $C_{1-10}$alkyl; and $R_5$ and $R_6$ are each independently H or $C_{1-10}$alkyl. Preferably, X is C or N; $R_1$ is $NR_7R_8$ wherein $R_7$ is $C_{1-10}$alkylpiperazinylphenyl, piperidinyl$C_{1-10}$alkyl, $C_{1-10}$alkylpiperazinylC1-10alkyl or $C_{1-10}$alkylpiperazinylcarbonylphenyl and $R_8$ is H; $R_2$ is H, halo or phenyl; $R_3$ and $R_4$ are each independently $C_{1-10}$alkyl; and $R_5$ and $R_6$ are each independently H or $C_{1-10}$alkyl. More preferably, X is C or N; $R_1$ is $NR_7R_8$ wherein $R_7$ is ethylpiperazinylphenyl, methylpiperazinylethyl or ethylpiperazinylcarbonylphenyl and $R_8$ is H; $R_2$ is H, phenyl or $C_1$; $R_3$ and $R_4$ are each independently $C_{1-10}$alkyl; and $R_5$ and $R_6$ are each independently H or $C_{1-10}$alkyl.

In some embodiments of formula (I), the compounds include but are not limited to the following:
1-(6-((4-(4-ethylpiperazin-1-yl)phenyl)amino)pyrimidin-4-yl)-1-methyl-3-(2,4,6-trichloro-3,5-dimethoxyphenyl) urea;
1-(6-((4-(4-ethylpiperazin-1-yl)phenyl)amino)-2-phenylpyrimidin-4-yl)-1-methyl-3-(2,4,6-trichloro-3,5-dimethoxyphenyl)urea;
1-(4-((4-(4-ethylpiperazin-1-yl)phenyl)amino)-1,3,5-triazin-2-yl)-1-methyl-3-(2,4,6-trichloro-3,5-dimethoxyphenyl)urea;
1-(4-chloro-6-((4-(4-ethylpiperazin-1-yl)phenyl)amino)-1,3,5-triazin-2-yl)-1-methyl-3-(2,4,6-trichloro-3,5-dimethoxyphenyl)urea;
1-methyl-1-(6-((2-(piperidin-1-yl)ethyl)amino)pyrimidin-4-yl)-3-(2,4,6-trichloro-3,5-dimethoxyphenyl)urea;
1-methyl-1-(6-((2-(4-methylpiperazin-1-yl)ethyl)amino)pyrimidin-4-yl)-3-(2,4,6-trichloro-3,5-dimethoxyphenyl) urea;

1-(6-((4-(4-ethylpiperazine-1-carbonyl)phenyl)amino)pyrimidin-4-yl)-1-methyl-3-(2,4,6-trichloro-3,5-dimethoxyphenyl)urea;

1-(6-(4-(4-ethylpiperazin-1-yl)phenyl)pyrimidin-4-yl)-1-methyl-3-(2,4,6-trichloro-3,5-dimethoxyphenyl)urea;

1-methyl-1-(6-phenylpyrimidin-4-yl)-3-(2,4,6-trichloro-3,5-dimethoxyphenyl)urea;

1-(6-(4-methoxyphenyl)pyrimidin-4-yl)-1-methyl-3-(2,4,6-trichloro-3,5-dimethoxyphenyl)urea;

1-(6-(4-fluorophenyl)pyrimidin-4-yl)-1-methyl-3-(2,4,6-trichloro-3,5-dimethoxyphenyl)urea;

1-(6-(4-chlorophenyl)pyrimidin-4-yl)-1-methyl-3-(2,4,6-trichloro-3,5-dimethoxyphenyl)urea;

1-(6-(4-cyanophenyl)pyrimidin-4-yl)-1-methyl-3-(2,4,6-trichloro-3,5-dimethoxyphenyl)urea;

1-(6-(3-cyanophenyl)pyrimidin-4-yl)-1-methyl-3-(2,4,6-trichloro-3,5-dimethoxyphenyl)urea;

1-methyl-1-(6-(3-nitrophenyl)pyrimidin-4-yl)-3-(2,4,6-trichloro-3,5-dimethoxyphenyl)urea;

1-(6-(furan-2-yl)pyrimidin-4-yl)-1-methyl-3-(2,4,6-trichloro-3,5-dimethoxyphenyl)urea;

1-methyl-1-(6-(pyridin-3-yl)pyrimidin-4-yl)-3-(2,4,6-trichloro-3,5-dimethoxyphenyl)urea; and 1-methyl-1-(6-(pyridin-4-yl)pyrimidin-4-yl)-3-(2,4,6-trichloro-3,5-dimethoxyphenyl)urea;

or a tautomer or stereoisomer thereof, or a solvate, prodrug or a pharmaceutically acceptable salt thereof.

In a further embodiment, the compound of the invention is 1-(4-((4-(4-ethylpiperazin-1-yl)phenyl)amino)-1,3,5-triazin-2-yl)-1-methyl-3-(2,4,6-trichloro-3,5-dimethoxyphenyl)urea,

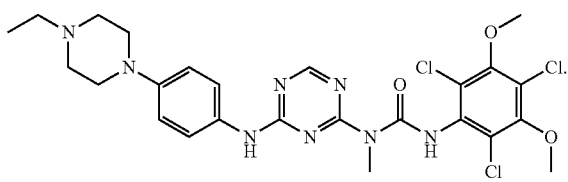 [SMILES: CCN1CCN(c2ccc(Nc3ncnc(N(C)C(=O)Nc4c(Cl)c(OC)c(Cl)c(OC)c4Cl)n3)cc2)CC1]

The compounds of the present invention can be prepared using methods known to those skilled in the art in view of this disclosure. For example, the preferred compounds of the invention can be prepared as shown in the following schemes:

Scheme 1

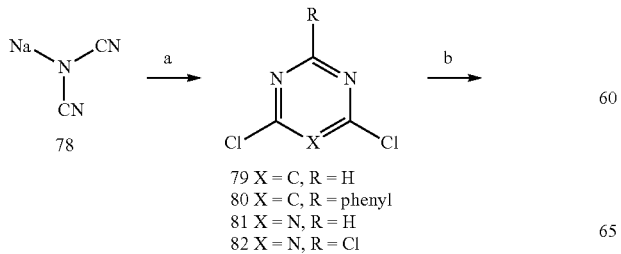

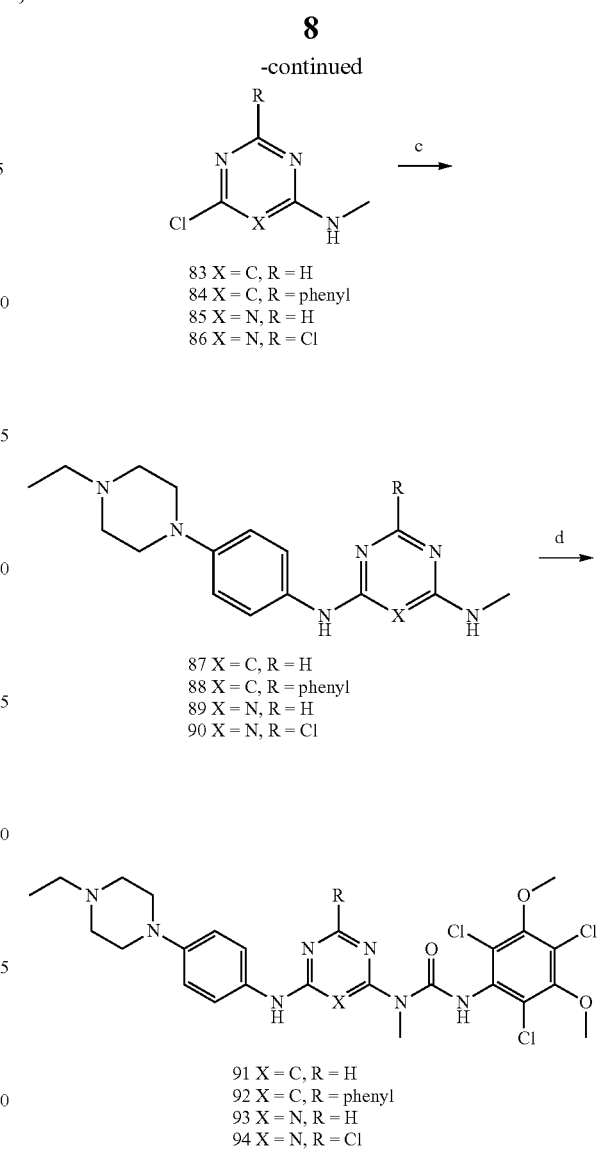

*Reagents and condition (a) conc. HCl (aq.), H₂O, -78° C. then POCl₃, DMF, DCM, 0° C. to r.t. (b) 2M Methylamine in THF, IPA, r.t. (c) 5, AcOH/H₂O, reflux (d) 14, triphosgene, p-dioxane, toluene, reflux then toluene, reflux Scheme 2

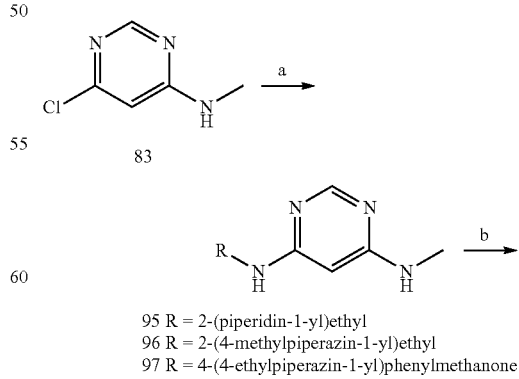

95 R = 2-(piperidin-1-yl)ethyl
96 R = 2-(4-methylpiperazin-1-yl)ethyl
97 R = 4-(4-ethylpiperazin-1-yl)phenylmethanone -continued

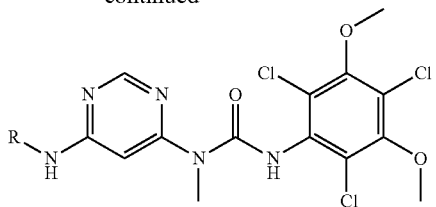

98 R = 2-(piperidin-1-yl)ethyl
99 R = 2-(4-methylpiperazin-1-yl)ethyl
100 R = 4-(4-ethylpiperazin-1-yl)phenylmethanone

*Reagents and condition
(a) substituted amine, AcOH/H$_2$O, reflux (b) 14, triphosgene, p-dioxane, toluene, reflux then toluene, reflux Scheme 3

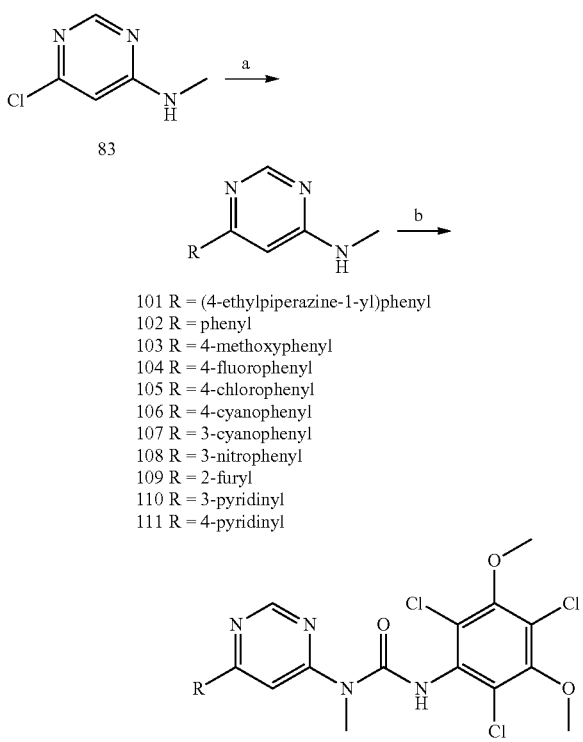

101 R = (4-ethylpiperazine-1-yl)phenyl
102 R = phenyl
103 R = 4-methoxyphenyl
104 R = 4-fluorophenyl
105 R = 4-chlorophenyl
106 R = 4-cyanophenyl
107 R = 3-cyanophenyl
108 R = 3-nitrophenyl
109 R = 2-furyl
110 R = 3-pyridinyl
111 R = 4-pyridinyl 112 R = (4-ethylpiperazine-1-yl)phenyl
113 R = phenyl
114 R = 4-methoxyphenyl
115 R = 4-fluorophenyl
116 R = 4-chlorophenyl
117 R = 4-cyanophenyl
118 R = 3-cyanophenyl
119 R = 3-nitrophenyl
120 R = 2-furyl
121 R = 3-pyridinyl
122 R = 4-pyridinyl

*Reagents and condition
(a) substituted boronic acid, PdCl$_2$(dppf), Cs$_2$CO$_3$, p-dioxane/H$_2$O, reflux
(b) 14, triphosgene, p-dioxane, toluene, reflux then toluene, reflux In another aspect, the invention provides a pharmaceutical composition, comprising a compound of the invention and a pharmaceutically acceptable carrier. When employed as a pharmaceutical, the compound of the invention is typically administered in the form of a pharmaceutical composition. Such compositions can be prepared in a manner well known in the pharmaceutical art and comprise at least one active compound. Generally, the compound of the invention is administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

In one embodiment, the compound is present in the composition in an amount that is effective to achieve its intended therapeutic purpose. While individual needs may vary, a determination of optimal ranges of effective amounts of each compound is within the skill of the art. Typically, the compounds may be administered to a mammal, e.g. a human, orally at a dose of from about 0.1 to about 100 mg per kg body weight of the mammal, or an equivalent amount of a pharmaceutically acceptable salt, prodrug or solvate thereof, per day to treat, prevent or ameliorate the particular disorder. Preferably, the dose ranges from about 0.1 to about 90 mg, about 0.1 to about 80 mg, about 0.1 to about 70 mg, about 0.1 to about 60 mg, about 0.1 to about 50 mg, about 0.1 to about 40 mg, about 0.1 to about 30 mg, about 0.1 to about 20 mg, about 0.1 to about 10 mg, about 0.1 to about 5 mg, about 0.5 to about 100 mg, about 0.5 to about 90 mg, about 0.5 to about 80 mg, about 0.5 to about 70 mg, about 0.5 to about 60 mg, about 0.5 to about 50 mg, about 0.5 to about 40 mg, about 0.5 to about 30 mg, about 0.5 to about 20 mg, about 0.5 to about 10 mg, about 0.5 to about 5 mg, about 1 to about 100 mg, about 1 to about 90 mg, about 1 to about 80 mg, about 1 to about 70 mg, about 1 to about 60 mg, about 1 to about 50 mg, about 1 to about 40 mg, about 1 to about 30 mg, about 1 to about 20 mg, about 1 to about 10 mg, about 5 to about 100 mg, about 5 to about 90 mg, about 5 to about 80 mg, about 5 to about 70 mg, about 5 to about 60 mg, about 5 to about 50 mg, about 5 to about 40 mg, about 5 to about 30 mg, about 5 to about 20 mg, about 5 to about 10 mg, about 10 to about 100, about 20 to about 100, about 30 to about 100, about 40 to about 100, about 50 to about 100, about 60 to about 100, about 70 to about 100, about 80 to about 100, about 5 to about 90, about 10 to about 90, about 10 to about 80, about 10 to about 70, about 10 to about 60, about 10 to about 50, about 10 to about 40, about 10 to about 30, about 20 to about 90, about 20 to about 80, about 20 to about 70, about 20 to about 60, about 20 to about 50, about 20 to about 40, about 30 to about 90, about 30 to about 80, about 30 to about 70, about 30 to about 60, about 30 to about 50, about 40 to about 90, about 40 to about 80, about 40 to about 60, about 50 to about 90, about 50 to about 80, about 50 to about 70 per kg body weight of the mammal, or an equivalent amount of a pharmaceutically acceptable salt, prodrug or solvate thereof, per day. A useful oral dose of a compound of the present invention administered to a mammal is from about 5 to about 100 mg per kg body weight of the mammal (the preferred dose is as mentioned above), or an equivalent amount of the pharmaceutically acceptable salt, prodrug or solvate thereof. For intramuscular injection, the dose is typically about one-half of the oral dose.

A unit oral dose may comprise from about 0.1 to about 100 mg, and preferably about 1 to about 80 mg of a compound. The unit dose can be administered one or more times daily, e.g. as one or more tablets or capsules, each containing from about 0.01 mg to about 50 mg of the compound, or an equivalent amount of a pharmaceutically acceptable salt, prodrug or solvate thereof.

The pharmaceutical compositions of the invention can be administered by a variety of routes including oral, rectal, transdermal, subcutaneous, intra-articular, intravenous, intramuscular, and intranasal. Depending on the intended route of delivery, the compound of this invention is preferably formulated as either an injectable or oral compositions.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient, vehicle or carrier. Typical unit dosage forms include prefilled, premeasured ampules or syringes of the liquid compositions or pills, tablets, capsules or the like in the case of solid compositions.

Pharmaceutical compositions within the scope of the present invention include all compositions where a compound of the present invention is combined with a pharmaceutically acceptable carrier. In a preferred embodiment, the compound is present in the composition in an amount that is effective to achieve its intended therapeutic purpose. While individual needs may vary, determination of optimal ranges of effective amounts of each compound is within the skill of the art.

The compounds and/or pharmaceutical compositions of the present invention may be useful in combination with one or more second therapeutic agents, and exemplary pharmaceutical composition can include or exclude any of the one or more second therapeutic agents described herein, particularly therapeutic agents suitable for the treatment and/or prevention of the conditions and diseases presented previously. For example in the cancer treatment, the second therapeutic agent can be a mitotic inhibitor (such as taxanes (preferably paclitaxel, docetaxel), vinca alkaloids (preferably, vinblastine, vincristine, vindesine and vinorelbine) and vepesid; an anthracycline antibiotic, (such as doxorubicin, daunorubicin, daunorubicin, epirubicin, idarubicin, valrubicin and mitoxantrone); a nucleoside analog (such as gemcitabine); an EGFR inhibitor (such as gefitinib and erlotinib); a folate antimetabolite (such as trimethoprim, pyrimethamine and pemetrexed); cisplatin and carboplatin. Examples of the second therapeutic agent that can be included or excluded in the exemplary compounds and/or exemplary pharmaceutical compositions can include, but are not limited to, tamoxifen, taxol, vinblastine, etoposide (VP-16), adriamycin, 5-fluorouracil (5FU), camptothecin, actinomycin-D, mitomycin C, combretastatin(s), more particularly docetaxel (taxotere), cisplatin (CDDP), cyclophosphamide, doxorubicin, methotrexate, paclitaxel and vincristine, and derivatives and prodrugs thereof.

Further useful exemplary second therapeutic agents include compounds that interfere with DNA replication, mitosis, chromosomal segregation and/or tubulin activity. Such compounds include adriamycin, also known as doxorubicin, etoposide, verapamil, podophyllotoxin(s), combretastatin(s) and the like. Agents that disrupt the synthesis and fidelity of polynucleotide precursors may also be used. Particularly useful are agents that have undergone extensive testing and are readily available. As such, agents such as 5-fluorouracil (5-FU) are preferentially used in neoplastic tissue, making this agent particularly useful for targeting to neoplastic cells.

In another aspect, the present invention provides a method for inhibiting, preventing or treating a cancer in a subject, comprising administering to the subject an effective amount of the compound and/or pharmaceutical composition of the invention. Such method includes administering of a compound of the present invention to a subject in an amount sufficient to treat the condition. For example, the cancers include but are not limited to those selected from the group consisting of: neuroblastoma; lung cancer; bile duct cancer; non-small cell lung carcinoma; hepatocellular carcinoma; head and neck squamous cell carcinoma; squamous cell cervical carcinoma; lymphoma; nasopharyngeal carcinoma; gastric cancer; colon cancer; uterine cervical carcinoma; gall bladder cancer; prostate cancer; breast cancer; testicular germ cell tumors; colorectal cancer; glioma; thyroid cancer; basal cell carcinoma; gastrointestinal stromal cancer; hepatoblastoma; endometrial cancer; ovarian cancer; pancreatic cancer; renal cell cancer, Kaposi's sarcoma, chronic leukemia, sarcoma, rectal cancer, throat cancer, melanoma, colon cancer, bladder cancer, mastocytoma, mammary carcinoma, mammary adenocarcinoma, pharyngeal squamous cell carcinoma, testicular cancer, gastrointestinal cancer, liver cancer, stomach cancer, myeloma and urothelial cancer. Preferably, the cancer is bladder cancer and hepatocellular carcinoma. The compounds and pharmaceutical compositions of the invention can be used as FGFR inhibitors and thus are effective in treatment or prevention of FGFR-activated cancers. Accordingly, the invention provides a method for inhibiting, preventing or treating a FGFR-activated cancer in a subject, comprising administering to the subject an effective amount of the compound of the invention.

For oral administration, suitable pharmaceutical compositions of the invention include powders, granules, pills, tablets, lozenges, chews, gels, and capsules as well as liquids, syrups, suspensions, elixirs, and emulsions. These compositions may also include anti-oxidants, flavorants, preservatives, suspending, thickening and emulsifying agents, colorants, flavoring agents and other pharmaceutically acceptable additives. Formulations for oral administration may be formulated to be immediate release or modified release, where modified release includes delayed, sustained, pulsed, controlled, targeted and programmed release.

For parenteral administration, the compounds and pharmaceutical composition of the present invention are administered directly into the blood stream, into muscle, or into an internal organ via an intravenous, intraarterial, intraperitoneal, intramuscular, subcutaneous or other injection or infusion. Parenteral formulations may be prepared in aqueous injection solutions which may contain, in addition to the compound of the invention, buffers, antioxidants, bacteriostats, salts, carbohydrates, and other additives commonly employed in such solutions. Parenteral administrations may be immediate release or modified release (such as an injected or implanted depot).

Compounds and pharmaceutical compositions of the present invention may also be administered topically, (intra) dermally, or transdermally to the skin or mucosa. Typical formulations include gels, hydrogels, lotions, solutions, creams, ointments, dressings, foams, skin patches, wafers, implants and microemulsions. Compounds of the present invention may also be administered via inhalation or intanasal administration, such as with a dry powder, an aerosol spray or as drops. Additional routes of administration for exemplary compounds and compositions of the present invention include intravaginal and rectal (by means of a suppository, pessary or enema), ocular and aural.

The following examples are given for the purpose of illustrating the present invention and shall not be construed as being limitations to the scope or spirit of the invention.

EXAMPLES

Example 1 Preparation of 2,4-dichloro-1,3,5-triazine (81)

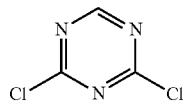

A mixture of 78 (3.0 g, 33.70 mmol) was dissolved in $H_2O$ (13 ml) and then added to another flask which filled with conc. HCl (15 ml) at −78° C. The resulting mixture was stirred at −78° C. for 15 min then heated to −35° C. for 15 min. Then, the mixture was cool to the 0° C. and filtered to produce the precipitant. Take another flask filled with DM (10 ml) at room temperature and $POCl_3$ (1.84 ml, 19.71 mmol) and DMF (1.53 ml, 19.71 mmol) were added to the flask at 0° C. After stirred for a while, the resulting mixture was added to the above precipitant portion-wisely and then stirred at room temperature for overnight. The reaction was quenched by water and then the mixture was extracted by ethyl acetate (30 ml×3). The residue was purified by flash column over silica gel (ethyl acetate: n-Hexane=1:4, Rf=0.63) to afford 81 (0.64 g, 13.13%) as a white solid. $^1$H-NMR (300 MHz, $CDCl_3$): δ 8.90 (s, 1H).

Example 2 Preparation of 6-chloro-N-methylpyrimidin-4-amine (83)

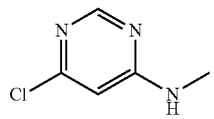

A mixture of 79 (0.50 g, 3.36 mmol) and IPA (1.5 ml) was stirred for a while and then 2M methylamine in THF (4.2 ml, 8.40 mmol) was added thereto at 0° C. The resulting mixture was back to room temperature under stirring for overnight. The reaction was quenched by water and then the mixture was extracted by ethyl acetate (30 ml×3). The residue was purified by flash column over silica gel (ethyl acetate:n-Hexane=1:2, Rf=0.20) to afford 83 (0.47 g, 97.43%) as a pale yellow solid. $^1$H-NMR (300 MHz, $CDCl_3$): δ 2.95 (d, J=5.1 Hz, 3H), 5.26 (br, 1H), 6.34 (s, 1H), 8.34 (s, 1H).

Example 3 Preparation of 6-chloro-N-methyl-2-phenylpyrimidin-4-amine (84)

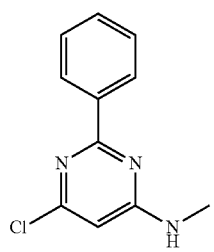

A mixture of 80 (0.25 g, 1.11 mmol) and IPA (3 ml) was stirred for a while and then 2M methylamine in THF (1.39 ml, 2.78 mmol) was added thereto at 0° C. The resulting mixture was back to room temperature under stirring for overnight. The reaction was quenched by water and then the mixture was extracted by ethyl acetate (30 ml×3). The residue was purified by flash column over silica gel (ethyl acetate:n-Hexane=1:4, Rf=0.18) to afford 84 (0.22 g, 90.23%) as a pale yellow solid. $^1$H-NMR (300 MHz, $CDCl_3$): δ 3.02 (d, J=4.2 Hz, 3H), 5.09 (br, 1H), 6.26 (s, 1H), 7.42-7.46 (m, 3H), 8.35-8.37 (m, 2H).

Example 4 Preparation of 4-chloro-N-methyl-1,3,5-triazin-2-amine (85)

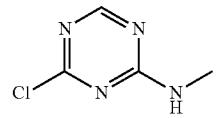

A mixture of 81 (0.10 g, 0.67 mmol) and IPA (3 ml) was stirred for a while and then 2M methylamine in THF (0.67 ml, 1.34 mmol) was added thereto at 0° C. The resulting mixture was back to room temperature under stirring for overnight. The reaction was quenched by water and the mixture was extracted by ethyl acetate (30 ml×3). The residue was purified by flash column over silica gel (ethyl acetate:n-Hexane=1:1, Rf=0.50) to afford 85 (0.07 g, 72.27%) as a pale white solid. $^1$H-NMR (300 MHz, $CDCl_3$): δ 3.03-3.06 (m, 3H), 5.71 (br, 1H), 8.36 (d, J=42.0 Hz, 1H),

Example 5 Preparation of 4,6-dichloro-N-methyl-1,3,5-triazin-2-amine (86)

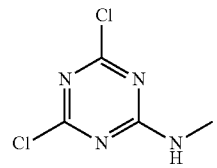

A mixture of 82 (2.0 g, 10.85 mmol), DIPEA (3.78 ml, 21.70 mmol) and THF (40 ml) was stirred at −78° C. for a while then methylamine HCl (0.72 g, 10.85 mmol) was added thereto at −78° C. under stirring for 1 hr. The reaction was quenched by water and the mixture was extracted by dichloromethane (30 ml×3). The residue was filtered to afford 86 (0.56 g, 28.83%) as a white solid. $^1$H-NMR (300 MHz, $CDCl_3$): δ 3.08 (d, J=5.1 Hz, 3H), 6.35 (br, 1H).

Example 6 Preparation of $N^4$-(4-(4-ethylpiperazin-1-yl)phenyl)-$N^6$-methylpyrimidine-4,6-diamine (87)

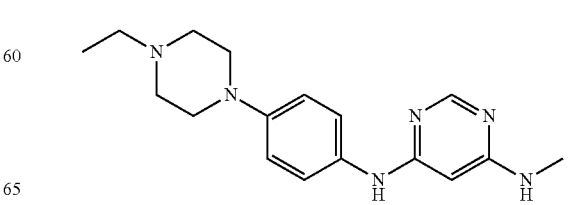

A mixture of 5 (0.49 g, 2.39 mmol), H$_2$O (0.75 ml) and AcOH (3 ml) was mixed with the 83 (0.15 g, 3.13 mmol) and refluxed for overnight. The reaction was quenched by saturated NaHCO$_3$ (aq.) and the mixture was extracted by ethyl acetate (30 ml×3). The residue was purified by flash column over silica gel (dichloromethane:methanol=9:1, Rf=0.25) to afford 87 (0.60 g, 80.20%) as a pale orange solid. $^1$H-NMR (300 MHz, CDCl$_3$): δ 1.16 (t, J=7.2 Hz, 3H), 2.48 (q, J=7.2 Hz, 2H), 2.64 (t, J=5.1 Hz, 4H), 2.81 (d, J=5.4 Hz, 3H), 3.22 (t, J=5.1 Hz, 4H), 4.86 (s, 1H), 5.54 (s, 1H), 6.69 (s, 1H), 6.95 (d, J=9.0 Hz, 2H), 7.18 (d, J=8.7 Hz, 2H), 8.14 (s, 1H).

Example 7 Preparation of N$^4$-(4-(4-ethylpiperazin-1-yl)phenyl)-N$^6$-methyl-2-phenylpyrimidine-4,6-diamine (88)

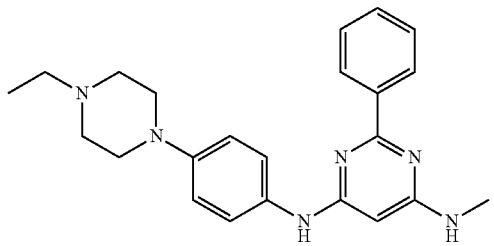 [SMILES: CCN1CCN(c2ccc(Nc3cc(NC)nc(-c4ccccc4)n3)cc2)CC1]

A mixture of 5 (0.16 g, 0.77 mmol), H$_2$O (0.4 ml) and AcOH (1.6 ml) was mixed with the 84 (0.22 g, 1.00 mmol) and then refluxed for overnight. The reaction was quenched by saturated NaHCO$_3$ (aq.) and the mixture was extracted by ethyl acetate (30 ml×3). The residue was purified by flash column over silica gel (dichloromethane:methanol=9:1, Rf=0.35) to afford 88 (0.22 g, 73.54%) as a pale yellow solid. $^1$H-NMR (500 MHz, CDCl$_3$): δ 1.16 (t, J=7.5 Hz, 3H), 2.52 (q, J=7.5 Hz, 2H), 2.66 (t, J=5.0 Hz, 4H), 2.88 (d, J=5.0 Hz, 3H), 3.25 (t, J=5.0 Hz, 4H), 4.84 (s, 1H), 5.51 (s, 1H), 6.51 (s, 1H), 6.95 (d, J=8.5 Hz, 2H), 7.23 (d, J=8.5 Hz, 2H), 7.42-7.43 (m, 3H), 8.31-8.33 (m, 2H).

Example 8 Preparation of N$^2$-(4-(4-ethylpiperazin-1-yl)phenyl)-N$^4$-methyl-1,3,5-triazine-2,4-diamine (89)

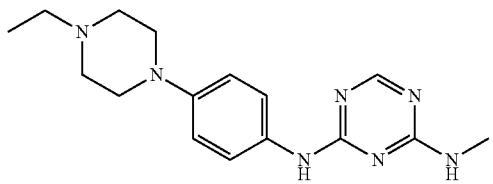 [SMILES: CCN1CCN(c2ccc(Nc3ncnc(NC)n3)cc2)CC1]

A mixture of 5 (0.10 g, 0.48 mmol), DIPEA (0.08 ml, 0.48 mmol) and EtOH (5 ml) was mixed with the 85 (0.07 g, 0.48 mmol) and refluxed for 2.5 hrs. The reaction was quenched by saturated NaHCO$_3$ (aq.) and the mixture was extracted by ethyl acetate (30 ml×3). The residue was purified by flash column over silica gel (dichloromethane:methanol=9:1, Rf=0.28) to afford 89 (0.05 g, 33.24%) as a pale yellow solid. $^1$H-NMR (300 MHz, CDCl$_3$): δ 1.13 (t, J=7.2 Hz, 3H), 2.46 (q, J=7.2 Hz, 2H), 2.62 (t, J=5.1 Hz, 4H), 2.98 (d, J=5.1 Hz, 3H), 3.19 (t, J=5.1 Hz, 4H), 5.17-5.29 (m, 1H), 5.55 (br, 1H), 6.91 (d, J=8.7 Hz, 2H), 7.37 (d, J=8.1 Hz, 1H), 7.46 (s, 1H), 8.20 (d, J=44.7 Hz, 1H).

Example 9 Preparation of 6-chloro-N-(4-(4-ethylpiperazin-1-yl)phenyl)-N$^4$-methyl-1,3,5-triazine-2,4-diamine (90)

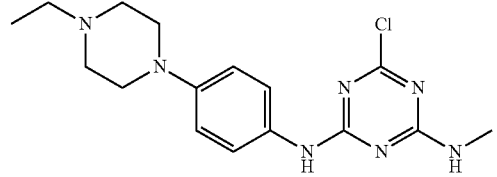 [SMILES: CCN1CCN(c2ccc(Nc3nc(Cl)nc(NC)n3)cc2)CC1]

A mixture of 5 (0.1 g, 0.56 mmol), DIPEA (0.10 ml, 0.56 mmol) and acetonitrile (3 ml) was mixed with the 86 (0.10 g, 0.56 mmol) and then stirred at room temperature for overnight. The reaction was quenched by saturated NaHCO$_3$ (aq.) and the mixture was extracted by ethyl acetate (30 ml×3). The residue was purified by flash column over silica gel (dichloromethane; methanol=15:1, Rf=0.18) to afford 90 (0.06 g, 30.80%) as a brown solid. $^1$H-NMR (300 MHz, CDCl$_3$): δ 1.15 (t, J=7.2 Hz, 3H), 2.51 (q, J=7.2 Hz, 2H), 2.64 (s, 4H), 3.01 (d, J=7.2 Hz, 3H), 3.22 (t, J=5.4 Hz, 4H), 5.30 (br, 1H), 5.74 (br, 1H), 6.88-6.94 (m, 2H), 7.11 (s, 1H), 7.35 (d, J=9.0 Hz, 1H), 7.37-7.48 (s, 1H).

Example 10 Preparation of 1-(6-((4-(4-ethylpiperazin-1-yl)phenyl)amino)pyrimidin-4-yl)-1-methyl-3-(2,4,6-trichloro-3,5-dimethoxyphenyl)urea (91)

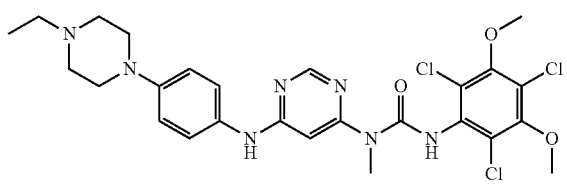 [SMILES: CCN1CCN(c2ccc(Nc3cc(N(C)C(=O)Nc4c(Cl)c(OC)c(Cl)c(OC)c4Cl)ncn3)cc2)CC1]

A mixture of 14 (0.25 g, 0.97 mmol) and p-dioxane (7 ml) was mixed with the triphosgene (0.48 g, 1.61 mmol) dissolved in toluene (3 ml) and then stirred and refluxed for overnight. The solvent was directly removed out and the resulting precipitate was dissolved in toluene (10 ml). The 87 (0.25 g, 0.81 mmol) was added to the resulting mixture and stirred and refluxed for overnight. The reaction was quenched by saturated NaHCO$_3$ (aq.) and the mixture was extracted by ethyl acetate (30 ml×3). The residue was purified by flash column over silica gel (dichloromethane: methanol=6:1, Rf=0.35) to afford 91 (0.10 g, 20.75%) as a pale yellow solid. $^1$H-NMR (300 MHz, CDCl$_3$): δ 1.14 (t, J=7.2 Hz, 3H), 2.49 (q, J=7.2 Hz, 2H), 2.63 (t, J=5.1 Hz, 4H), 3.26 (t, J=5.4 Hz, 4H), 3.30 (s, 3H), 3.91 (s, 6H), 6.10 (s, 1H), 6.97 (d, J=9.0 Hz, 2H), 7.20 (d, J=9.0 Hz, 2H), 8.34 (s, 1H), 12.76 (s, 1H).

Example 11 Preparation of 1-(6-((4-(4-ethylpiperazin-1-yl)phenyl)amino)-2-phenylpyrimidin-4-yl)-1-methyl-3-(2,4,6-trichloro-3,5-dimethoxyphenyl)urea (92)

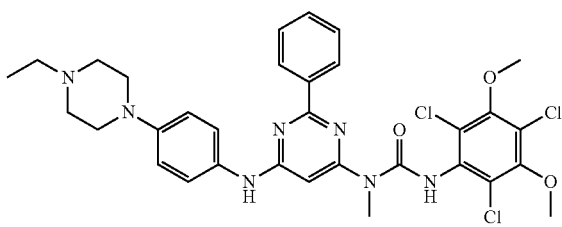 [SMILES: CCN1CCN(c2ccc(Nc3cc(N(C)C(=O)Nc4c(Cl)c(OC)c(Cl)c(OC)c4Cl)nc(-c4ccccc4)n3)cc2)CC1]

A mixture of 14 (0.20 g, 0.76 mmol) and p-dioxane (7 ml) was mixed with the triphosgene (0.38 g, 1.26 mmol) dissolved in toluene (3 ml) and then stirred and refluxed for overnight. The solvent was directly removed out and the resulting precipitate was dissolved in toluene (10 ml). The 88 (0.25 g, 0.64 mmol) was added to the mixture and stirred and refluxed for overnight. The reaction was quenched by saturated NaHCO$_3$ (aq.) and the mixture was extracted by ethyl acetate (30 ml×3). The residue was purified by flash column over silica gel (dichloromethane:methanol=6:1, Rf=0.35) to afford 92 (0.04 g, 9.31%) as a pale yellow solid. $^1$H-NMR (300 MHz, CDCl$_3$): δ 1.16 (t, J=7.5 Hz, 3H), 2.51 (q, J=7.2 Hz, 2H), 2.66 (t, J=5.1 Hz, 4H), 3.27 (t, J=5.1 Hz, 4H), 3.83 (s, 3H), 3.97 (s, 6H), 6.99 (d, J=9.3 Hz, 2H), 7.49-7.56 (m, 3H), 7.67 (d, J=9.0 Hz, 2H), 8.48-8.51 (m, 2H), 10.72 (s, 1H).

Example 12 Preparation of 1-(4-((4-(4-ethylpiperazin-1-yl)phenyl)amino)-1,3,5-triazin-2-yl)-1-methyl-3-(2,4,6-trichloro-3,5-dimethoxyphenyl)urea (93)

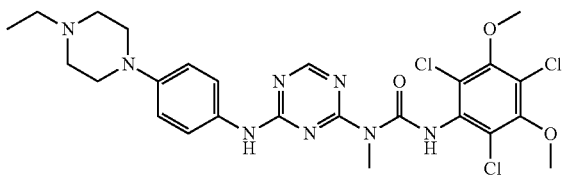 [SMILES: CCN1CCN(c2ccc(Nc3ncnc(N(C)C(=O)Nc4c(Cl)c(OC)c(Cl)c(OC)c4Cl)n3)cc2)CC1]

A mixture of 14 (0.39 g, 1.52 mmol) and p-dioxane (7 ml) was mixed with triphosgene (0.75 g, 2.52 mmol) dissolved in toluene (3 ml) and then stirred and refluxed for overnight. The solvent was directly removed out and the resulting precipitate was dissolved in toluene (10 ml). The 89 (0.40 g, 1.28 mmol) was added to the mixture and stirred and refluxed for overnight. The reaction was quenched by saturated NaHCO$_3$ (aq.) and the mixture was extracted by ethyl acetate (30 ml×3). The residue was purified by flash column over silica gel (dichloromethane:methanol=15:1, Rf=0.35) to afford 93 (0.12 g, 15.73%) as a pale yellow solid. $^1$H-NMR (500 MHz, CDCl$_3$+CD$_3$OD): δ 1.02 (t, J=7.5 Hz, 3H), 2.37 (q, J=7.5 Hz, 2H), 2.46-2.53 (m, 4H), 2.89-3.09 (m, 4H), 3.41 (s, 3H), 3.76 (s, 3H), 3.79 (s, 3H), 6.59-6.84 (m, 2H), 7.14-7.31 (m, 2H), 8.32 (s, 1H).

Example 13 Preparation of 1-(4-chloro-6-((4-(4-ethylpiperazin-1-yl)phenyl)amino)-1,3,5-triazin-2-yl)-1-methyl-3-(2,4,6-trichloro-3,5-dimethoxyphenyl)urea (94)

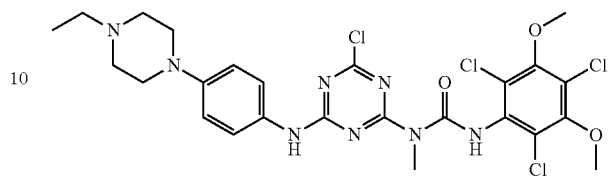

A mixture of 14 (0.26 g, 1.03 mmol) and p-dioxane (7 ml) was mixed with triphosgene (0.51 g, 1.71 mmol) dissolved in toluene (3 ml) and then stirred and refluxed for overnight. The solvent was directly removed out and the resulting precipitate was dissolved in toluene (10 ml). The 90 (0.30 g, 0.86 mmol) was added to the mixture and then stirred and refluxed for overnight. The reaction was quenched by saturated NaHCO$_3$ (aq.) and the mixture was extracted by ethyl acetate (30 ml×3). The residue was purified by flash column over silica gel (dichloromethane; methanol=9:1, Rf=0.25) to afford 94 (0.04 g, 7.38%) as a pale yellow solid. $^1$H-NMR (500 MHz, CDCl$_3$): δ 1.12 (t, J=7.0 Hz, 3H), 2.46-2.62 (m, 6H), 2.97-3.24 (m, 4H), 3.53 (s, 3H), 3.90 (s, 6H), 6.65-6.95 (br, 2H), 7.04-7.46 (m, 2H), 11.50 (s, 1H).

Example 14 Preparation of N$^4$-methyl-N$^6$-(2-(piperidin-1-yl)ethyl)pyrimidine-4,6-diamine (95)

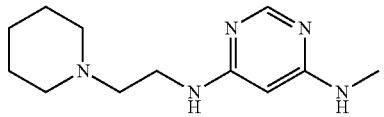 [SMILES: CNc1cc(NCCN2CCCCC2)ncn1]

A mixture of 83 (0.05 g, 0.35 mmol) and n-BuOH (2 ml) was mixed with the TEA (0.12 ml, 0.88 mmol) and 2-(piperidin-1-yl)ethanamine (0.05 ml, 0.35 mmol) and then stirred and refluxed for overnight. The residue was purified by flash column over silica gel (dichloromethane:methanol=15:1, Rf=0.15) to afford 95 (0.04 g, 48.56%) as a pale yellow solid. $^1$H-NMR (300 MHz, DMSO-d$_6$): δ 1.47-1.49 (m, 4H), 1.57-1.59 (m, 3H), 2.70 (d, J=5.1 Hz, 3H), 3.46 (br, 4H), 5.50 (s, 1H), 6.51 (d, J=5.4 Hz, 1H), 7.94 (s, 1H).

Example 15 Preparation of N$^4$-methyl-N$^6$-(2-(4-methylpiperazin-1-yl)ethyl)pyrimidine-4,6-diamine (96)

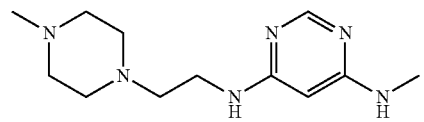

A mixture of 83 (0.05 g, 0.35 mmol) and 2-(4-methylpiperazin-1-yl)ethanamine (0.35 g, 2.45 mmol) was stirred at 120° C. for overnight. The residue was purified by flash column over silica gel (dichloromethane:methanol=6:1, Rf=0.13) to afford 96 (0.02 g, 22.83%) as a pale yellow solid. ¹H-NMR (500 MHz, CD₃OD): δ 2.28 (s, 3H), 2.53 (br, 4H), 2.59 (t, J=6.5 Hz, 2H), 2.80 (s, 3H), 3.29-3.36 (m, 2H), 5.39 (s, 1H), 7.87 (s, 1H).

Example 16 Preparation of (4-ethylpiperazin-1-yl) (4-((6-(methylamino)pyrimidin-4-yl)amino)phenyl) methanone (97)

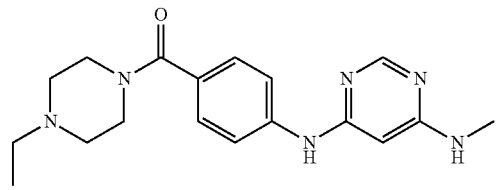 [SMILES: CCN1CCN(C(=O)c2ccc(Nc3cc(NC)ncn3)cc2)CC1]

A mixture of 1-ethylpiperazine (0.10 g, 0.88 mmol) and acetonitrile (3 ml) was mixed with potassium carbonate (0.18 g, 1.32 mmol) and 4-nitrobenzoyl chloride (0.16 g, 1.32 mmol) and then stirred at room temperature for 4 hrs. The residue was purified by flash column over silica gel (dichloromethane:methanol=9:1, Rf=0.20) to afford the product. The 10% Pd/C was added to the mixture of the above product and MeOH (5 ml) as catalyst and the mixture was then stirred under hydrogen gas at room temperature for 2 hs. The mixture was filtered to get the filtrate and then the solvent was removed out to get the crude product. A mixture of 83 (0.14 g, 0.95 mmol), H₂O (0.5 ml) and AcOH (2 ml) was added to the above crude product and then stirred and refluxed for overnight. The reaction was quenched by saturated NaHCO₃ (aq.) and the mixture was extracted by ethyl acetate (30 ml×3). The residue was purified by flash column over silica gel (dichloromethane:methanol=9:1, Rf=0.06) to afford 97 (0.07 g, 28.17%) as a brown solid. ¹H-NMR (300 MHz, CDCl₃): δ 1.07 (t, J=5.1 Hz, 3H), 2.47 (t, J=5.1 Hz, 6H), 2.78 (s, 3H), 3.62 (br, 4H), 5.77 (s, 1H), 7.32 (d, J=5.4 Hz, 2H), 7.52 (d, J=5.4 Hz, 2H), 8.04 (s, 1H).

Example 17 Preparation of 1-methyl-1-(6-((2-(piperidin-1-yl)ethyl)amino)pyrimidin-4-yl)-3-(2,4,6-trichloro-3,5-dimethoxyphenyl)urea (98)

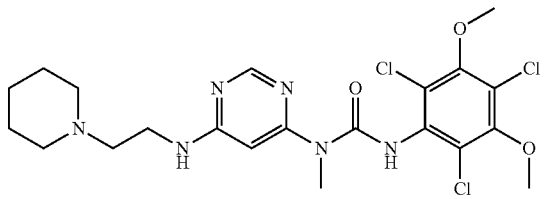 [SMILES: COc1c(Cl)c(NC(=O)N(C)c2cc(NCCN3CCCCC3)ncn2)c(Cl)c(OC)c1Cl]

A mixture of 14 (0.16 g, 0.61 mmol) and p-dioxane (7 ml) was nixed with triphosgene (0.30 g, 1.01 mmol) dissolved in toluene (3 ml) and then stirred and refluxed for overnight. The solvent was directly removed out and the resulting precipitate was dissolved in toluene (10 ml). The 95 (0.12 g, 0.51 mmol) was added to the mixture and the mixture was stirred and refluxed for overnight. The reaction was quenched by saturated NaHCO₃ (aq.) and the mixture was extracted by ethyl acetate (30 ml×3). The residue was purified by flash column over silica gel (dichloromethane:methanol=15:1, Rf=0.35) to afford 98 (0.06 g, 22.72%) as a pale yellow solid. ¹H-NMR (300 MHz, CDCl₃): δ 1.54 (br, 3H), 1.65 (br, 7H), 3.42 (d, J=5.1 Hz, 3H), 3.67 (br, 4H), 3.90 (d, J=5.1 Hz, 6H), 6.00 (s, 1H), 8.32 (s, 1H), 12.82 (s, 1H).

Example 18 Preparation of 1-methyl-1-(6-((2-(4-methylpiperazin-1-yl)ethyl)amino)pyrimidin-4-yl)-3-(2,4,6-trichloro-3,5-dimethoxyphenyl)urea (99)

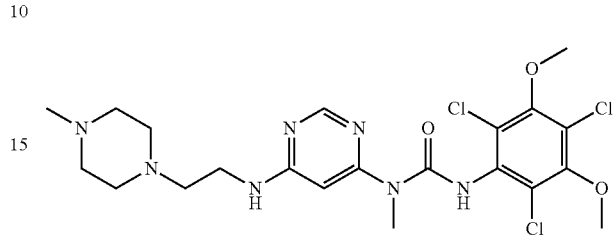

A mixture of 14 (0.09 g, 0.33 mmol) and p-dioxane (7 ml) was mixed with triphosgene (0.16 g, 0.55 mmol) dissolved in toluene (3 ml) and then the mixture was stirred and refluxed for overnight. The solvent was directly removed out and the resulting precipitate was dissolved in toluene (10 ml). The 96 (0.07 g, 0.28 mmol) was added to the mixture and then the mixture was stirred and refluxed for overnight. The reaction was quenched by saturated NaHCO₃ (aq.) and the mixture was extracted by ethyl acetate (30 ml×3). The residue was purified by flash column over silica gel (dichloromethane:methanol=9:1, Rf=0.20) to afford 99 (0.03 g, 20.11%) as a pale yellow solid. ¹H-NMR (300 MHz, CDCl₃): δ 2.67 (s, 3H), 2.52 (t, J=5.1 Hz, 4H), 3.43 (br, 4H), 3.73 (t, J=5.1 Hz, 4H), 3.90 (s, 6H), 6.01 (s, 1H), 8.33 (m, 1H), 12.77 (s, 1H).

Example 19 Preparation of 1-(6-((4-(4-ethylpiperazine-1-carbonyl)phenyl)amino)pyrimidin-4-yl)-1-methyl-3-(2,4,6-trichloro-3,5-dimethoxyphenyl)urea (100) 19-2370-2B

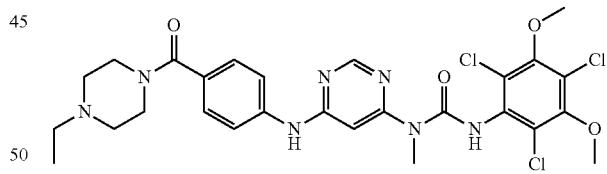

A mixture of 14 (0.36 g, 1.40 mmol) and p-dioxane (7 ml) was mixed with triphosgene (0.70 g, 2.32 mmol) dissolved in toluene (3 ml) and then the mixture was stirred and refluxed for overnight. The solvent was directly removed out and the resulting precipitate was dissolved in toluene (10 ml). The 97 (0.40 g, 1.18 mmol) was added to the mixture and the mixture was stirred and refluxed for overnight. The reaction was quenched by saturated NaHCO₃ (aq.) and the mixture was extracted by ethyl acetate (30 ml×3). The residue was purified by flash column over silica gel (dichloromethane:methanol=19:1, Rf=0.25) to afford 100 (0.01 g, 1.36%) as a pale yellow solid. ¹H-NMR (300 MHz, CDCl₃): δ 1.18 (s, 3H), 2.56 (t, J=5.1 Hz, 6H), 3.41 (s, 3H), 3.81 (m, 4H) 3.92 (br, 1H), 6.34 (s, 1H), 7.03 (s, 5H), 7.47 (s, 1H), 8.47 (s, 1H), 12.60 (s, 1H).

Example 20 Preparation of 6-(4-(4-ethylpiperazin-1-yl)phenyl)-N-methylpyrimidin-4-amine (101)

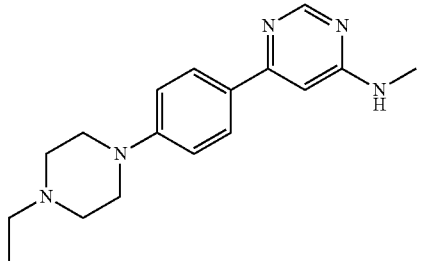 [SMILES: CCN1CCN(c2ccc(-c3cc(NC)ncn3)cc2)CC1]

A mixture of 1-(4-bromophenyl)piperazine (0.15 g, 0.62 mmol) and acetone (5 ml) was mixed with potassium carbonate (0.17 g, 1.24 mmol) and ethyl iodide (0.08 ml, 1.00 mmol) and then stirred at room temperature for 4 hrs. The residue was purified by flash column over silica gel (dichloromethane:methanol=9:1, Rf=0.43) to get the product. PdCl$_2$dppf (0.04 g, 0.06 mmol), potassium acetate (0.55 g, 5.58 mmol) and bispinacolactoboron (0.71 g, 2.79 mmol) were added to the mixture of above product and p-dioxane (10 ml) and the resulting mixture was stirred and refluxed for overnight. The residue was purified by flash column over silica gel (dichloromethane:methanol=9:1, Rf=0.48) to get the product. The PdCl$_2$dppf (0.04 g, 0.06 mmol), potassium acetate (0.55 g, 5.58 mmol) and bispinacolactoboron (0.71 g, 2.79 mmol) were assed to the mixture of 83 (0.06 g, 0.41 mmol), H$_2$O (1 ml) and p-dioxane (4 ml) and the resulting mixture was then stirred and refluxed for overnight. The reaction was quenched by saturated NaHCO$_3$ (aq.) and the mixture was extracted by ethyl acetate (30 ml×3). The residue was purified by flash column over silica gel (dichloromethane:methanol=19:1, Rf=0.19) to afford 101 (0.08 g, 65.61%) as a pale yellow solid. $^1$H-NMR (500 MHz, CDCl$_3$): δ 1.16 (t, J=7.0 Hz, 3H), 2.52 (d, J=7.0 Hz, 2H), 2.65 (s, 4H), 3.00 (d, J=5.0 Hz, 3H), 3.35 (s, 4H), 4.92 (s, 1H), 6.62 (s, 1H), 6.97 (d, J=7.0 Hz, 2H), 7.93 (d, J=9.0 Hz, 2H), 8.59 (s, 1H).

Example 21 Preparation of N-methyl-6-phenylpyrimidin-4-amine (102)

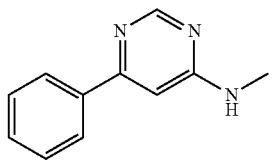

The PdCl$_2$dppf (0.14 g, 0.20 mmol), cesium carbonate (1.27 g, 3.90 mmol) and phenylboronic acid (0.24 g, 1.95 mmol) were added to the mixture of 83 (0.28 g, 1.95 mmol), H$_2$O (1.5 ml) and p-dioxane (6 ml) and then the resulting mixture was stirred and refluxed for overnight. The reaction was quenched by saturated NaHCO$_3$ (aq.) and the mixture was extracted by ethyl acetate (30 ml×3). The residue was purified by flash column over silica gel (ethyl acetate:n-Hexane=1:2, Rf=0.30) to afford 102 (0.25 g, 69.21%) as a pale yellow solid. $^1$H-NMR (300 MHz, CD$_3$OD): δ 2.95 (s, 3H), 6.84 (s, 1H), 7.45-7.48 (m, 3H), 7.89 (s, 2H), 8.45 (s, 1H).

Example 22 Preparation of 6-(4-methoxyphenyl)-N-methylpyrimidin-4-amine (103)

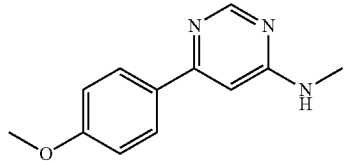

The PdCl$_2$dppf (0.14 g, 0.20 mmol), cesium carbonate (1.27 g, 3.90 mmol) and 4-methoxybenzeneboronic acid (0.30 g, 1.95 mmol) were added to the mixture of 83 (0.28 g, 1.95 mmol), H$_2$O (1.5 ml) and p-dioxane (6 ml) and the resulting mixture was then stirred and refluxed for overnight. The reaction was quenched by saturated NaHCO$_3$ (aq.) and the mixture was extracted by ethyl acetate (30 ml×3). The residue was purified by flash column over silica gel (ethyl acetate:n-Hexane=1:1, Rf=0.18) to afford 103 (0.30 g, 71.47%) as a pale yellow solid. $^1$H-NMR (300 MHz, CDCl$_3$): δ 3.01 (d, J=5.1 Hz, 3H), 3.86 (s, 3H), 5.04 (s, 1H), 6.64 (s, 1H), 6.98 (d, J=9.0 Hz, 2H), 7.96 (d, J=8.7 Hz, 2H), 8.61 (s, 1H).

Example 23 Preparation of 6-(4-fluorophenyl)-N-methylpyrimidin-4-amine (104)

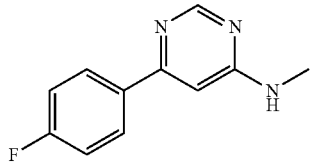

The PdCl$_2$dppf (0.14 g, 0.20 mmol), cesium carbonate (1.27 g, 3.90 mmol) and 4-fluorobenzeneboronic acid (0.27 g, 1.95 mmol) were added to the mixture of 83 (0.28 g, 1.95 mmol), H$_2$O (1.5 ml) and p-dioxane (6 ml) then the resulting mixture was stirred and refluxed for overnight. The reaction was quenched by saturated NaHCO$_3$ (aq.) and the mixture was extracted by ethyl acetate (30 ml×3). The residue was purified by flash column over silica gel (ethyl acetate:n-Hexane=1:2, Rf=0.15) to afford 104 (0.16 g, 40.38%) as a pale yellow solid. $^1$H-NMR (300 MHz, CDCl$_3$): δ 3.02 (d, J=5.1 Hz, 3H), 5.10 (s, 1H), 6.65 (s, 1H), 7.12-7.18 (m, 2H), 7.96-8.01 (m, 2H), 8.63 (s, 1H).

Example 24 Preparation of 6-(4-chlorophenyl)-N-methylpyrimidin-4-amine (105)

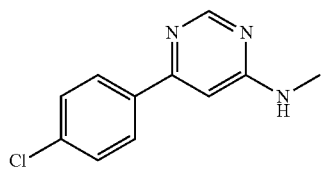

The PdCl$_2$dppf (0.14 g, 0.20 mmol), cesium carbonate (1.27 g, 3.90 mmol) and 4-chlorobenzeneboronic acid (0.30 g, 1.95 mmol) were added to the mixture of 83 (0.28 g, 1.95 mmol), H$_2$O (1.5 ml) and p-dioxane (6 ml) and the resulting mixture was then stirred and refluxed for overnight. The reaction was quenched by saturated NaHCO$_3$ (aq.) and the mixture was extracted by ethyl acetate (30 ml×3). The residue was purified by flash column over silica gel (ethyl acetate:n-Hexane=1:2, Rf=0.06) to afford 105 (0.20 g, 46.69%) as a pale yellow solid. $^1$H-NMR (300 MHz, CDCl$_3$): δ 3.02 (d, J=5.1 Hz, 3H), 5.11 (s, 1H), 6.66 (s, 1H), 7.44 (d, J=8.7 Hz, 2H), 7.93 (d, J=8.7 Hz, 2H), 8.63 (s, 1H).

Example 25 Preparation of 4-(6-(methylamino)pyrimidin-4-yl)benzonitrile (106)

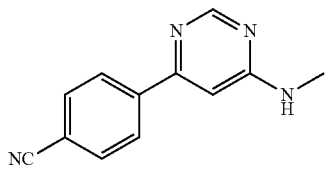 [SMILES: CNc1cc(-c2ccc(C#N)cc2)ncn1]

The PdCl$_2$dppf (0.14 g, 0.20 mmol), cesium carbonate (1.27 g, 3.90 mmol) and 4-cyanobenzeneboronic acid (0.29 g, 1.95 mmol) were added to the mixture of 83 (0.28 g, 1.95 mmol), H$_2$O (1.5 ml) and p-dioxane (6 ml) and the resulting mixture was then stirred and refluxed for overnight. The reaction was quenched by saturated NaHCO$_3$ (aq.) and the mixture was extracted by ethyl acetate (30 ml×3). The residue was purified by flash column over silica gel (ethyl acetate:n-Hexane=1:2, Rf=0.23) to afford 106 (0.30 g, 73.18%) as a pale yellow solid. $^1$H-NMR (300 MHz, CD$_3$OD): δ 3.05 (d, J=5.4 Hz, 3H), 5.21 (s, 1H), 6.73 (s, 1H), 7.76 (d, J=8.7 Hz, 2H), 8.10 (d, J=8.7 Hz, 2H), 8.67 (s, 1H).

Example 26 Preparation of 3-(6-(methylamino)pyrimidin-4-yl)benzonitrile (107)

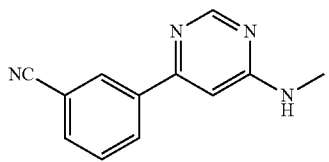 [SMILES: CNc1cc(-c2cccc(C#N)c2)ncn1]

The PdCl$_2$dppf (0.14 g, 0.20 mmol), cesium carbonate (1.27 g, 3.90 mmol) and 3-cyanobenzeneboronic acid (0.29 g, 1.95 mmol) were added to the mixture of 83 (0.28 g, 1.95 mmol), H$_2$O (1.5 ml) and p-dioxane (6 ml) and the resulting mixture was then stirred and refluxed for overnight. The reaction was quenched by saturated NaHCO$_3$ (aq.) and the mixture was extracted by ethyl acetate (30 ml×3). The residue was purified by flash column over silica gel (ethyl acetate:n-Hexane=1:1, Rf=0.13) to afford 107 (0.33 g, 80.45%) as a pale yellow solid. $^1$H-NMR (300 MHz, CD$_3$OD): δ 2.97 (s, 3H), 6.93 (s, 1H), 7.67 (t, J=7.8 Hz, 1H), 7.83 (d, J=7.8 Hz, 1H), 8.23 (d, J=8.7 Hz, 1H), 8.30 (s, 1H), 8.49 (s, 1H).

Example 27 Preparation of N-methyl-6-(3-nitrophenyl)pyrimidin-4-amine (108)

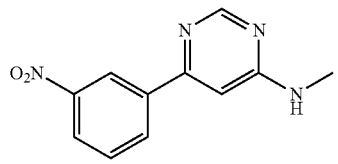 [SMILES: CNc1cc(-c2cccc([N+](=O)[O-])c2)ncn1]

The PdCl$_2$dppf (0.14 g, 0.20 mmol), cesium carbonate (1.27 g, 3.90 mmol) and 3-nitrobenzeneboronic acid (0.33 g, 1.95 mmol) were added to the mixture of 83 (0.28 g, 1.95 mmol), H$_2$O (1.5 ml) and p-dioxane (6 ml) and the resulting mixture was then stirred and refluxed for overnight. The reaction was quenched by saturated NaHCO$_3$ (aq.) and the mixture was extracted by ethyl acetate (30 ml×3). The residue was purified by flash column over silica gel (ethyl acetate:n-Hexane=1:1, Rf=0.38) to afford 108 (0.19 g, 42.32%) as a pale yellow solid. $^1$H-NMR (300 MHz, CD$_3$OD): δ 2.98 (s, 3H), 6.98 (s, 1H), 7.74 (t, J=8.1 Hz, 1H), 8.34 (d, J=8.1 Hz, 2H), 8.51 (s, 1H), 8.80 (s, 1H).

Example 28 Preparation of 6-(furan-2-yl)-N-methylpyrimidin-4-amine (109)

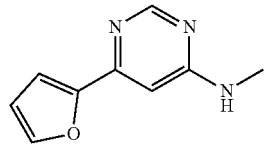

The PdCl$_2$dppf (0.14 g, 0.20 mmol), cesium carbonate (1.27 g, 3.90 mmol) and 2-furanboronic acid (0.22 g, 1.95 mmol) were added to the mixture of 83 (0.28 g, 1.95 mmol), H$_2$O (1.5 ml) and p-dioxane (6 ml) and the resulting mixture was then stirred and refluxed for overnight. The reaction was quenched by saturated NaHCO$_3$ (aq.) and the mixture was extracted by ethyl acetate (30 ml×3). The residue was purified by flash column over silica gel (ethyl acetate:n-Hexane=2:1, Rf=0.13) to afford 109 (0.10 g, 29.27%) as a pale yellow solid. $^1$H-NMR (300 MHz, CD$_3$OD): δ 3.01 (d, J=5.1 Hz, 3H), 5.11 (s, 1H), 6.55 (d, J=5.1 Hz, 1H), 6.68 (s, 1H), 7.17-7.18 (m, 1H), 7.55 (s, 1H), 8.54 (s, 1H).

Example 29 Preparation of N-methyl-6-(pyridin-3-yl)pyrimidin-4-amine (110)

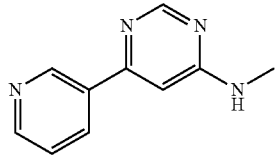

The PdCl$_2$dppf (0.03 g, 0.04 mmol), cesium carbonate (0.23 g, 0.70 mmol) and pyridine-3-boronic (0.04 g, 0.35 mmol) were added to the mixture of 83 (0.05 g, 0.35 mmol), H$_2$O (1 ml) and p-dioxane (4 ml) and the resulting mixture was then stirred and refluxed for overnight. The reaction was quenched by saturated NaHCO$_3$ (aq.) and the resulting mixture was extracted by ethyl acetate (30 ml×3). The residue was purified by flash column over silica gel (dichloromethane:methanol=9:1, Rf=0.44) to afford 110 (0.05 g, 76.72%) as a pale yellow solid. $^1$H-NMR (300 MHz, CD$_3$OD): δ 2.97 (s, 3H), 6.93 (s, 1H), 7.53-7.57 (m, 1H), 8.36 (d, J=8.1 Hz, 1H), 8.50 (s, 1H), 8.61-8.63 (m, 1H), 9.08 (s, 1H).

Example 30 Preparation of N-methyl-6-(pyridin-4-yl)pyrimidin-4-amine (111)

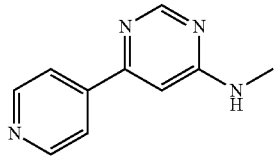

The PdCl$_2$dppf (0.18 g, 0.24 mmol), cesium carbonate (1.59 g, 4.88 mmol) and pyridine-4-boronic (0.30 g, 2.44 mmol) were added to the mixture of 83 (0.35 g, 2.44 mmol), H$_2$O (1.5 ml) and p-dioxane (6 ml) and the resulting mixture was then stirred and refluxed for overnight. The reaction was quenched by saturated NaHCO$_3$ (aq.) and the resulting mixture was extracted by ethyl acetate (30 ml×3). The residue was purified by flash column over silica gel (ethyl acetate:n-Hexane=1:2, Rf=0.10) to afford 111 (0.25 g, 55.02%) as a pale yellow solid. $^1$H-NMR (500 MHz, CD$_3$OD): δ 2.97 (s, 3H), 6.99 (s, 1H), 7.94 (s, 2H), 8.52 (s, 1H), 8.66 (d, J=6.5 Hz, 2H).

Example 31 Preparation of 1-(6-(4-(4-ethylpiperazin-1-yl)phenyl)pyrimidin-4-yl)-1-methyl-3-(2,4,6-trichloro-3,5-dimethoxyphenyl)urea (112)

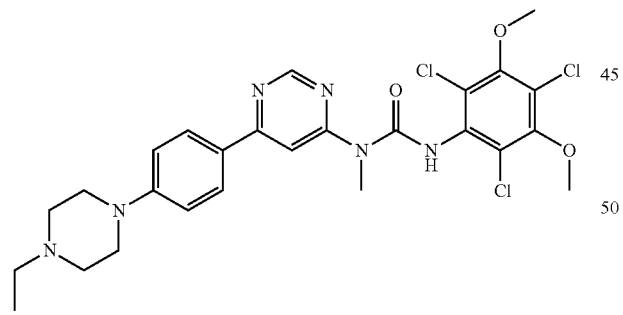

A mixture of 14 (0.24 g, 0.92 mmol) and p-dioxane (7 ml) was mixed with triphosgene (0.45 g, 1.53 mmol) dissolved in toluene (3 ml) and then the mixture was stirred and refluxed for overnight. The solvent was directly removed out and the precipitate was dissolved in toluene (10 ml). The 101 (0.23 g, 0.77 mmol) was added to the mixture and then the resulting mixture was stirred and refluxed for overnight. The reaction was quenched by saturated NaHCO$_3$ (aq.) and the resulting mixture was extracted by ethyl acetate (30 ml×3). The residue was purified by flash column over silica gel (dichloromethane:methanol=15:1, Rf=0.43) to afford 112 (0.07 g, 15.68%) as a pale yellow solid. $^1$H-NMR (500 MHz, CDCl$_3$): δ 1.14 (t, J=7.0 Hz, 3H), 2.49 (d, J=7.0 Hz, 2H), 2.63 (t, J=5.0 Hz, 4H), 3.38 (t, J=5.0 Hz, 4H), 3.57 (s, 3H), 3.91 (d, J=8.0 Hz, 6H), 7.00 (d, J=9.0 Hz, 2H), 8.02 (d, J=9.0 Hz, 2H), 8.83 (s, 1H), 12.59 (s, 1H).

Example 32 Preparation of 1-methyl-1-(6-phenylpyrimidin-4-yl)-3-(2,4,6-trichloro-3,5-dimethoxyphenyl)urea (113)

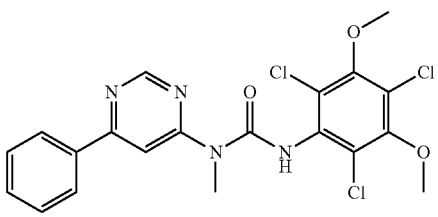 [SMILES: COc1c(Cl)c(NC(=O)N(C)c2cc(-c3ccccc3)ncn2)c(Cl)c(OC)c1Cl]

A mixture of 14 (0.25 g, 0.97 mmol) and p-dioxane (7 ml) was mixed with triphosgene (0.48 g, 1.61 mmol) dissolved in toluene (3 ml) and then the mixture was stirred and refluxed for overnight. The solvent was directly removed out and the resulting precipitate was dissolved in toluene (10 ml). The 102 (0.15 g, 0.81 mmol) was added to the mixture and the resulting mixture was stirred and refluxed for overnight. The reaction was quenched by saturated NaHCO$_3$ (aq.) and the mixture was extracted by ethyl acetate (30 ml×3). The residue was purified by flash column over silica gel (dichloromethane:methanol=9:1, Rf=0.55) to afford 113 (0.22 g, 58.07%) as a pale yellow solid. $^1$H-NMR (300 MHz, CDCl$_3$): δ 3.60 (s, 3H), 3.93 (s, 6H), 7.37 (s, 1H), 7.54-7.56 (m, 3H), 8.06-8.09 (m, 2H), 8.94 (s, 1H), 12.50 (s, 1H).

Example 33 Preparation of 1-(6-(4-methoxyphenyl) pyrimidin-4-yl)-1-methyl-3-(2,4,6-trichloro-3,5-dimethoxyphenyl)urea (114)

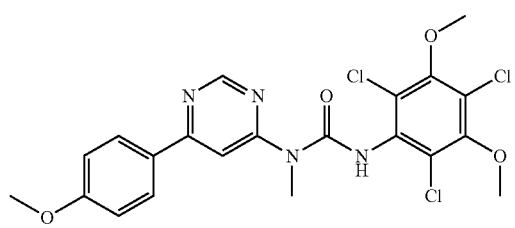

A mixture of 14 (0.25 g, 0.97 mmol) and p-dioxane (7 ml) was mixed with triphosgene (0.48 g, 1.61 mmol) dissolved in toluene (3 ml) and then the resulting mixture was stirred and refluxed for overnight. The solvent was directly removed out and the resulting precipitate was dissolved in toluene (10 ml). The 103 (0.17 g, 0.81 mmol) was added to the mixture and the resulting mixture was stirred and refluxed for overnight. The reaction was quenched by saturated NaHCO$_3$ (aq.) and the mixture was extracted by ethyl acetate (30 ml×3). The residue was purified by flash column over silica gel (ethyl acetate:n-Hexane=1:1, Rf=0.45) to afford 115 (0.23 g, 57.05%) as a pale yellow solid. $^1$H-NMR (300 MHz, CDCl$_3$): δ 3.60 (s, 3H), 3.90 (s, 3H), 3.93 (s, 6H), 7.04 (d, J=8.7 Hz, 2H), 7.30 (s, 1H), 8.06 (d, J=8.7 Hz, 2H), 8.88 (s, 1H), 12.54 (s, 1H).

Example 34 Preparation of 1-(6-(4-fluorophenyl) pyrimidin-4-yl)-1-methyl-3-(2,4,6-trichloro-3,5-dimethoxyphenyl)urea (115)

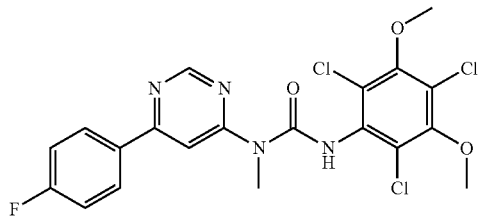 [SMILES: COc1c(Cl)c(NC(=O)N(C)c2cc(-c3ccc(F)cc3)ncn2)c(Cl)c(OC)c1Cl]

A mixture of 14 (0.25 g, 0.97 mmol) and p-dioxane (7 ml) was mixed with triphosgene (0.48 g, 1.61 mmol) dissolved in toluene (3 ml) and then the resulting mixture was stirred and refluxed for overnight. The solvent was directly removed out and the resulting precipitate was dissolved in toluene (10 ml). The 104 (0.16 g, 0.81 mmol) was added to the mixture and then the resulting mixture was stirred and refluxed for overnight. The reaction was quenched by saturated NaHCO$_3$ (aq.) and the mixture was extracted by ethyl acetate (30 ml×3). The residue was purified by flash column over silica gel (ethyl acetate:n-Hexane=1:2, Rf=0.33) to afford 115 (0.10 g, 25.42%) as a pale yellow solid. $^1$H-NMR (300 MHz, CDCl$_3$): δ 3.60 (s, 3H), 3.93 (s, 6H), 7.20-7.26 (m, 2H), 7.33 (s, 1H), 8.08-8.12 (m, 2H), 8.92 (s, 1H), 12.46 (s, 1H).

Example 35 Preparation of 1-(6-(4-chlorophenyl) pyrimidin-4-yl)-1-methyl-3-(2,4,6-trichloro-3,5-dimethoxyphenyl)urea (116)

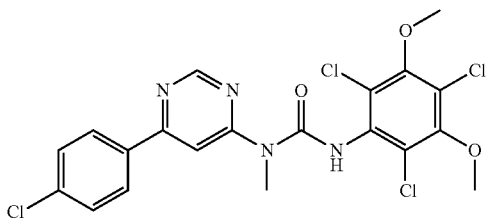 [SMILES: COc1c(Cl)c(NC(=O)N(C)c2cc(-c3ccc(Cl)cc3)ncn2)c(Cl)c(OC)c1Cl]

A mixture of 14 (0.25 g, 0.97 mmol) and p-dioxane (7 ml) was mixed with triphosgene (0.48 g, 1.61 mmol) dissolved in toluene (3 ml) and then the resulting mixture was stirred and refluxed for overnight. The solvent was directly removed out and the resulting precipitate was dissolved in toluene (10 ml). The 105 (0.15 g, 0.81 mmol) was added to the mixture and then the resulting mixture was stirred and refluxed for overnight. The reaction was quenched by saturated NaHCO$_3$ (aq.) and the mixture was extracted by ethyl acetate (30 ml×3). The residue was purified by flash column over silica gel (ethyl acetate:n-Hexane=1:2, Rf=0.38) to afford 116 (0.1 g, 27.04%) as a pale yellow solid. $^1$H-NMR (300 MHz, CDCl$_3$): δ 3.60 (s, 3H), 3.93 (s, 6H), 7.34 (s, 1H), 7.53 (d, J=8.7 Hz, 2H), 8.04 (d, J=8.7 Hz, 2H), 8.92 (s, 1H), 12.44 (s, 1H).

Example 36 Preparation of 1-(6-(4-cyanophenyl) pyrimidin-4-yl)-1-methyl-3-(2,4,6-trichloro-3,5-dimethoxyphenyl)urea (117)

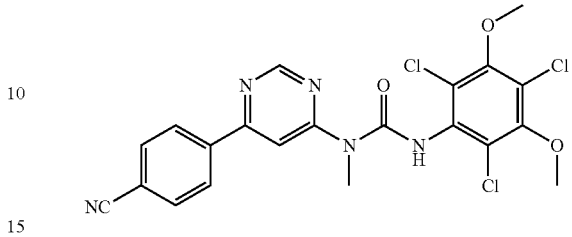

A mixture of 14 (0.25 g, 0.97 mmol) and p-dioxane (7 ml) was mixed with triphosgene (0.48 g, 1.61 mmol) dissolved in toluene (3 ml) and then the resulting mixture was stirred and refluxed for overnight. The solvent was directly removed out and the resulting precipitate was dissolved in toluene (10 ml). The 106 (0.17 g, 0.81 mmol) was added to the mixture and then the resulting mixture was stirred and refluxed for overnight. The reaction was quenched by saturated NaHCO$_3$ (aq.) and the mixture was extracted by ethyl acetate (30 ml×3). The residue was purified by flash column over silica gel (ethyl acetate:n-Hexane=1:2, Rf=0.23) to afford 117 (0.12 g, 30.07%) as a pale yellow solid. $^1$H-NMR (300 MHz, CDCl$_3$): δ 3.61 (s, 3H), 3.93 (s, 6H), 7.40 (s, 1H), 7.84 (d, J=5.4 Hz, 2H), 8.20 (d, J=8.7 Hz, 2H), 8.98 (s, 1H), 12.32 (s, 1H).

Example 37 Preparation of 1-(6-(3-cyanophenyl) pyrimidin-4-yl)-1-methyl-3-(2,4,6-trichloro-3,5-dimethoxyphenyl)urea (118)

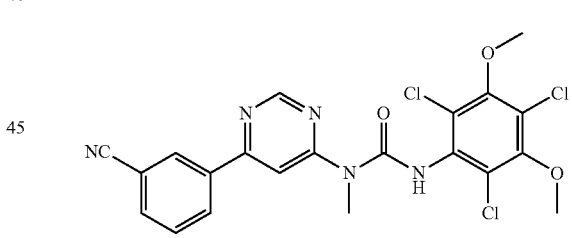

A mixture of 14 (0.25 g, 0.97 mmol) and p-dioxane (7 ml) was mixed with triphosgene (0.48 g, 1.61 mmol) dissolved in toluene (3 ml) and then the resulting mixture was stirred and refluxed for overnight. The solvent was directly removed out and the resulting precipitate was dissolved in toluene (10 ml). The 107 (0.17 g, 0.81 mmol) was added to the mixture and the resulting mixture was stirred and refluxed for overnight. The reaction was quenched by saturated NaHCO$_3$ (aq.) and the mixture was extracted by ethyl acetate (30 ml×3). The residue was purified by flash column over silica gel (ethyl acetate:n-Hexane=2:1, Rf=0.33) to afford 118 (0.12 g, 30.07%) as a pale yellow solid. $^1$H-NMR (300 MHz, CDCl$_3$): δ 3.60 (s, 3H), 3.92 (s, 6H), 7.36 (s, 1H), 7.66 (t, J=8.1 Hz, 1H), 7.81 (d, J=7.8 Hz, 1H), 8.30 (d, J=8.4 Hz, 1H), 8.39 (s, 1H), 8.95 (s, 1H), 12.33 (s, 1H).

Example 38 Preparation of 1-methyl-1-(6-(3-nitrophenyl)pyrimidin-4-yl)-3-(2,4,6-trichloro-3,5-dimethoxyphenyl)urea (119)

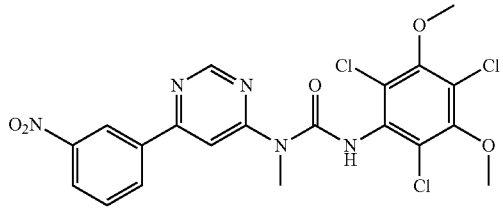 [SMILES: COc1c(Cl)c(NC(=O)N(C)c2cc(-c3cccc([N+](=O)[O-])c3)ncn2)c(Cl)c(OC)c1Cl]

A mixture of 14 (0.25 g, 0.97 mmol) and p-dioxane (7 ml) was mixed with triphosgene (0.48 g, 1.61 mmol) dissolved in toluene (3 ml) and then the resulting mixture was stirred and refluxed for overnight. The solvent was directly removed out and then the resulting precipitate was dissolved in toluene (10 ml). The 108 (0.19 g, 0.81 mmol) was added to the mixture and the resulting mixture was stirred and refluxed for overnight. The reaction was quenched by saturated $NaHCO_3$ (aq.) and the mixture was extracted by ethyl acetate (30 ml×3). The residue was purified by flash column over silica gel (ethyl acetate:n-Hexane=1:2, Rf=0.31) to afford 119 (0.06 g, 14.45%) as a pale yellow solid. $^1$H-NMR (300 MHz, $CDCl_3$): δ 3.64 (s, 3H), 3.93 (s, 6H), 7.44 (s, 1H), 7.75 (t, J=8.1 Hz, 1H), 8.39-8.47 (m, 2H), 8.94 (s, 1H), 8.99 (s, 1H), 12.36 (s, 1H).

Example 39 Preparation of 1-(6-(furan-2-yl)pyrimidin-4-yl)-1-methyl-3-(2,4,6-trichloro-3,5-dimethoxyphenyl)urea (120)

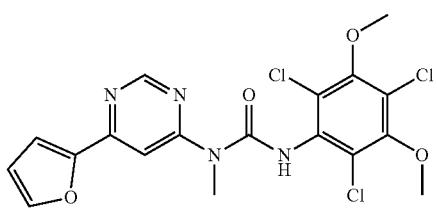 [SMILES: COc1c(Cl)c(NC(=O)N(C)c2cc(-c3ccco3)ncn2)c(Cl)c(OC)c1Cl]

A mixture of 14 (0.15 g, 0.58 mmol) and p-dioxane (7 ml) was mixed with triphosgene (0.29 g, 0.96 mmol) dissolved in toluene (3 ml) and then the resulting mixture was stirred and refluxed for overnight. The solvent was directly removed out and then the resulting precipitate was dissolved in toluene (10 ml). The 109 (0.09 g, 0.49 mmol) was added to the mixture and the resulting mixture was stirred and refluxed for overnight. The reaction was quenched by saturated $NaHCO_3$ (aq.) and the mixture was extracted by ethyl acetate (30 ml×3). The residue was purified by flash column over silica gel (ethyl acetate:n-Hexane=1:4, Rf=0.20) to afford 120 (0.05 g, 22.29%) as a pale yellow solid. $^1$H-NMR (300 MHz, $CDCl_3$): δ 3.58 (s, 3H), 3.93 (s, 6H), 6.62 (d, J=5.4 Hz, 1H), 7.33 (d, J=6.0 Hz, 2H), 7.64 (s, 1H), 8.80 (s, 1H), 12.47 (s, 1H).

Example 40 Preparation of 1-methyl-1-(6-(pyridin-3-yl)pyrimidin-4-yl)-3-(2,4,6-trichloro-3,5-dimethoxyphenyl)urea (121)

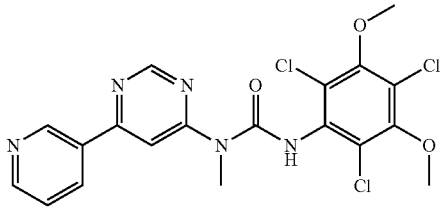 [SMILES: COc1c(Cl)c(NC(=O)N(C)c2cc(-c3cccnc3)ncn2)c(Cl)c(OC)c1Cl]

A mixture of 14 (0.25 g, 0.97 mmol) and p-dioxane (7 ml) was mixed with triphosgene (0.48 g, 1.61 mmol) dissolved in toluene (3 ml) and then the resulting mixture was stirred and refluxed for overnight. The solvent was directly removed out and the resulting precipitate was dissolved in toluene (10 ml). The 110 (0.15 g, 0.81 mmol) was added to the mixture and the resulting mixture was stirred and refluxed for overnight. The reaction was quenched by saturated $NaHCO_3$ (aq.) and the mixture was extracted by ethyl acetate (30 ml×3). The residue was purified by flash column over silica gel (dichloromethane:methanol=9:1, Rf=0.55) to afford 121 (0.04 g, 10.54%) as a pale yellow solid. $^1$H-NMR (300 MHz, $CDCl_3$): δ 3.62 (s, 3H), 3.93 (s, 6H), 7.41 (s, 1H), 7.50-7.54 (m, 1H), 8.44 (d, J=8.1 Hz, 1H), 8.79 (d, J=4.2 Hz, 1H), 8.97 (s, 1H), 9.29 (s, 1H), 12.38 (s, 1H).

Example 41 Preparation of 1-methyl-1-(6-(pyridin-4-yl)pyrimidin-4-yl)-3-(2,4,6-trichloro-3,5-dimethoxyphenyl)urea (122)

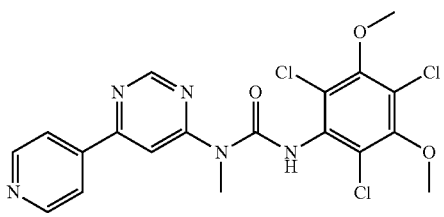 [SMILES: COc1c(Cl)c(NC(=O)N(C)c2cc(-c3ccncc3)ncn2)c(Cl)c(OC)c1Cl]

A mixture of 14 (0.25 g, 0.97 mmol) and p-dioxane (7 ml) was mixed with triphosgene (0.48 g, 1.61 mmol) dissolved in toluene (3 ml) and then the mixture was stirred and refluxed for overnight. The solvent was directly removed out and the resulting precipitate was dissolved in toluene (10 ml). The 110 (0.15 g, 0.81 mmol) was added to the mixture and the resulting mixture was stirred and refluxed for overnight. The reaction was quenched by saturated $NaHCO_3$ (aq.) and the mixture was extracted by ethyl acetate (30 ml×3). The residue was purified by flash column over silica gel (dichloromethane:methanol=9:1, Rf=0.30) to afford 122 (0.20 g, 52.68%) as a pale yellow solid. $^1$H-NMR (300 MHz, $CDCl_3$): δ 3.62 (s, 3H), 3.93 (s, 6H), 7.45 (s, 1H), 8.00 (d, J=6.0 Hz, 2H), 8.84 (d, J=4.8 Hz, 2H), 9.00 (s, 1H), 12.29 (s, 1H).

Example 42 Biological Assay—MTT Assay

Cells were cultured in RPMI-1640 (RT-112, KMS-11, SNU-16, HT-29, HCT-116, NCI—H520, Hep3B, PLC/PRF/

5, HL-60, MOLT-4) and DMEM (HepG2, MCF-7, MDA-MB-231) with 10% FBS (v/v) and Penicillin/Streptomycin (100 U/ml). FU-DDLS-1 cell line was maintained in DMEM:F12 medium with 10% FBS. LiSa-2 cell line was maintained in IMDM/RPMI-1640 in a 4:1 ratio supplemented with 10% FBS, 2 mmol/L L-glutamine, and 0.1 mg/mL gentamicin. Human umbilical vein endothelial cells (HUVECs) were grown to confluence on 1% collagen, and maintained in 90% Medium 199 with 25 U/ml heparin, 30 µg/ml endothelial cell growth supplement (ECGS) adjusted to contain 1.5 g/L sodium bicarbonate, 10% FBS and Penicillin/Streptomycin (100 U/ml) Cultures were maintained at 37° C. in a humidified atmosphere of 5% CO2/95% air.

Cells were seeded in 96-well plates (5,000 cells/well) and incubated overnight for attachment, and were then treated with indicated agents in 10% FBS-supplemented medium for 72 hours. The medium was replaced with MTT (0.5 mg/mL) at 37° C. for 1 hours. After removal of medium, the cells were lysed with 100 µL per well dimethyl sulfoxide (DMSO), and absorbance at 550 nm was measured with microplate reader. The relative cell viability (%) was expressed as a percentage relative to a DMSO control cells. The $IC_{50}$ value was determined as the concentration of compound needed to reduce cell viability to 50% of a DMSO control (Mean±S.D.). The testing compounds and their results of MTT assay are listed in the table below.

| | | Viability (% of control cells) | | | | | | | | |
|---|---|---|---|---|---|---|---|---|---|---|
| | | RT-112 (10 uM) | | RT-112 (5 uM) | | Hep3B (5 uM) | | PLC5 (5 uM) | | SNU-16 (5 uM) | |
| Code | Compound No. | Mean | S.D. | Mean | S.D. | Mean | S.D. | Mean | S.D. | Mean | S.D. |
| MPT0L090 | 91 | 12.7 | 1.0 | 52.6 | 5.3 | 47.1 | 6.5 | 72.6 | 3.8 | 27.5 | 0.7 |
| MPT0L146 | 92 | 29.7 | 3.8 | 100.8 | 5.8 | 94.3 | 1.2 | 88.0 | 0.4 | 83.4 | 13.3 |
| MPT0L145 | 93 | 8.5 | 0.7 | 33.4 | 7.5 | 66.2 | 6.4 | 20.6 | 1.1 | 36.9 | 7.9 |
| MPT0L183 | 94 | 3.4 | 0.3 | 15.8 | 1.8 | 43.3 | 2.8 | 45.0 | 4.1 | 28.2 | 1.7 |
| MPT0L182 | 112 | 8.6 | 2.0 | 95.6 | 3.7 | 96.3 | 4.7 | 78.3 | 7.8 | 63.2 | 4.6 |
| MPT0L149 | 113 | 82.3 | 1.3 | | | | | | | | |
| MPT0L153 | 114 | 43.0 | 3.4 | 63.8 | 13.9 | 93.6 | 6.6 | 91.3 | 3.6 | 76.2 | 2.4 |
| MPT0L155 | 115 | 44.4 | 2.2 | 92.6 | 1.6 | 72.8 | 1.1 | 55.3 | 3.9 | 80.5 | 6.1 |
| MPT0L156 | 116 | 34.8 | 1.5 | 98.3 | 2.2 | 54.3 | 3.1 | 44.4 | 4.8 | 76.7 | 8.1 |
| MPT0L152 | 117 | 55.3 | 1.2 | | | | | | | | |
| MPT0L150 | 118 | 75.0 | 4.3 | | | | | | | | |
| MPT0L151 | 119 | 63.8 | 0.8 | | | | | | | | |
| MPT0L154 | 120 | 76.1 | 8.0 | | | | | | | | |
| MPT0L147 | 121 | 85.0 | 2.7 | | | | | | | | |
| MPT0L148 | 122 | 89.3 | 3.5 | | | | | | | | |

Different cancer cell lines were used in MTT assay to test the anticancer activity of exemplary chlorobenzene substituted azaaryl compound (MPT0L145). A known compound, BJG398 (3-(2,6-Dichloro-3,5-dimethoxy-phenyl)-1-{6-[4-(4-ethylpiperazin-1-yl)-phenylamino]-pyrimidin-4-yl}-1-methyl-urea), was used as reference compound for comparison. The results show that MPT0L145 has unexpected efficacy in inhibiting exemplary bladder cancer and exemplary liver cancer over and much lower toxicity than BJG398

| Cell lines | Cancer type | MPT0L145 | BGJ-398 |
|---|---|---|---|
| RT-112 | Bladder | 1.63 ± 0.01 | 1.70 ± 0.05 |
| KMS-11 | Myeloma | 2.05 ± 0.11 | 0.2 ± 0.05 |
| FUDDLS | Sarcoma | 4.74 ± 0.49 | 1.45 ± 0.17 |
| LISA-2 | Sarcoma | 6.43 ± 0.26 | 6.13 ± 0.06 |
| SNU-16 | Gastric | 0.65 ± 0.07 | N/A |

-continued

| Cell lines | Cancer type | MPT0L145 | BGJ-398 |
|---|---|---|---|
| HT-29 | Colorectal | 2.49 ± 0.29 | 4.77 ± 0.14 |
| HCT-116 | Colorectal | 6.12 ± 0.01 | 3.98 ± 0.06 |
| HepG2 | Liver | 1.18 ± 0.16 | 5.84 ± 0.25 |
| PLC/PRF/5 | Liver | 1.48 ± 0.30 | 2.94 ± 0.11 |
| Hep3B | Liver | 6.47 ± 0.38 | 0.72 ± 0.12 |
| MCF-7 | Breast | 5.98 ± 0.68 | 5.07 ± 0.63 |
| MDA-MB-231 | Breast | 6.04 ± 0.26 | 4.27 ± 0.83 |
| HL-60 | AML | 4.72 ± 1.46 | N/A |
| MOLT-4 | ALL | 3.70 ± 0.20 | N/A |
| HUVEC | Normal cell | >8 | 0.05 ± 0.01 |

$IC_{50}$ (µM, Mean ± SD)

Example 42 Anti-Growth Activity of MPT0L145 in Bladder Cancer Cells

Figure 2:
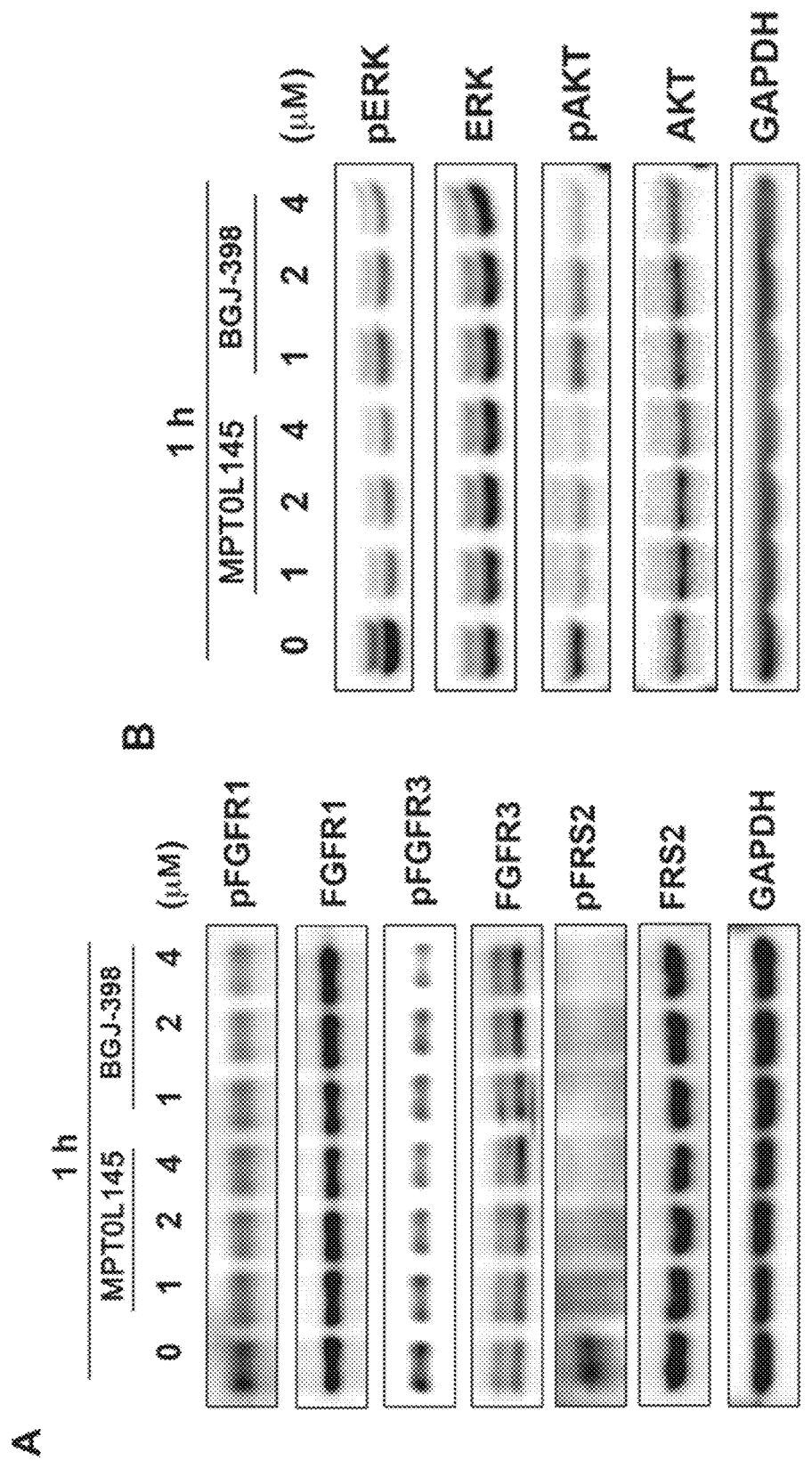
FIGS. 2A to 2D show the inhibition of FGFR signaling by MPT0L145 in RT-112 cells. A. RT-112 cells were treated with the indicated concentrations of MPT0L145 and BGJ-398 for 1 h and the levels of phosphorylated FGFR1, FGFR3 and FRS2 were detected via western blot. (B-D) Effects of MPT0L145 on FGFR downstream signaling. Cells were treated with the indicated concentrations of MPT0L145 or BGJ-398 for 1 h B. 4 h C. and 8 h D. Protein lysates were subjected to western blot analysis with the indicated antibodies.
Figure 2:
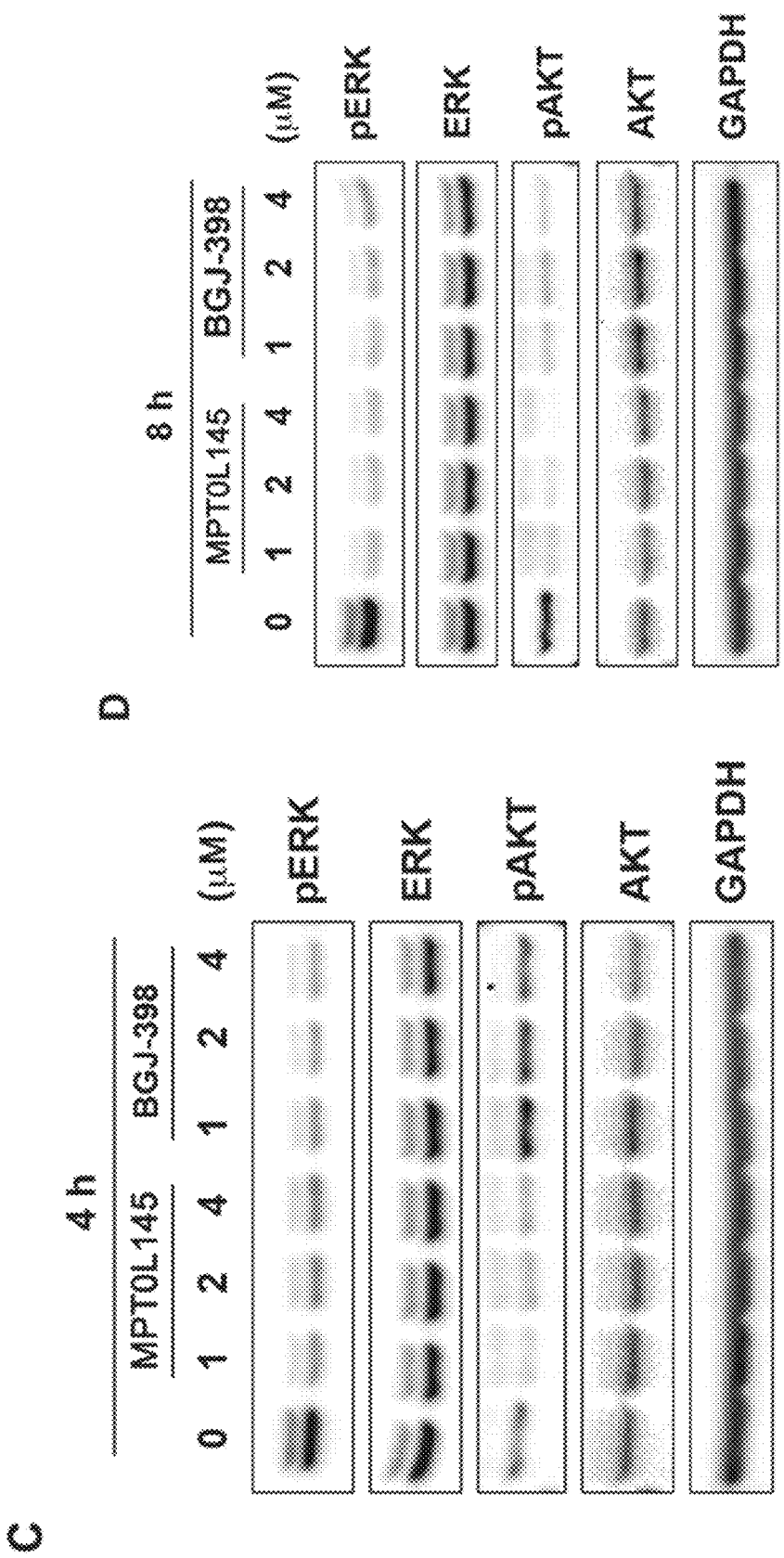

Activating mutations, gene fusion and overexpression of FGFR3 in bladder cancer have been documented, indicating that bladder cancer is a promising indication for the discovery of novel FGFR inhibitors. We examined the anti-growth effects of MPT0L145 on bladder cancer cells with different genetic background of FGFR3. Cells with the FGFR3-TACC3 fusion (RT-112, RT4) were more sensitive to MPT0L145 than those with normal FGFR3 status (T24) (FIG. 1A). Notably, MPT0L145 induced significantly lower toxicity in normal cells (HUVEC) than the known FGFR inhibitor, BGJ-398 (FIG. 1B). The $IC_{50}$ values of MPT0L145 in RT-112 and HUVEC were 11.1 µM and 0.05 µM, respectively. RT-112 cells reportedly rely on FGFRs for growth and are therefore chosen to confirm the effects of MPT0L145 on FGFR signaling [22, 23]. BGJ-398, a known selective inhibitor of FGFR1 to FGFR3, was included as a reference compound. The data revealed that MPT0L145 exerted inhibitory activity on auto-phosphorylation of FGFR1 and FGFR3 as well as its downstream docking protein, FRS2, in 1 h (FIG. 2A). The major downstream pathways of FGFRs are MAPK, PI3K/AKT, and PLC-γ. RT-112 cells, which express FGFR3-TACC3, are reportedly unable to activate PLCγ due to a deletion of the last exon of FGFR3. Next, we examined the kinetic effects of MPT0L145 on the signaling pathways downstream of FGFR from 1 to 8 h in RT-112 cells. MPT0L145 inhibited phosphorylation of ERK at 1 h in a concentration-dependent manner (FIG. 2B). The compound displayed better potency than BGJ-398 in inhibiting AKT phosphorylation from 1 to 4 h (FIG. 2B, 2C). The phosphorylation of ERK and AKT were fully repressed by MPT0L145 at 8 h (FIG. 2D). These data support the observed inhibitory effects of MPT0L145 on FGFR signaling pathways in bladder cancer cells.

Figure 3:
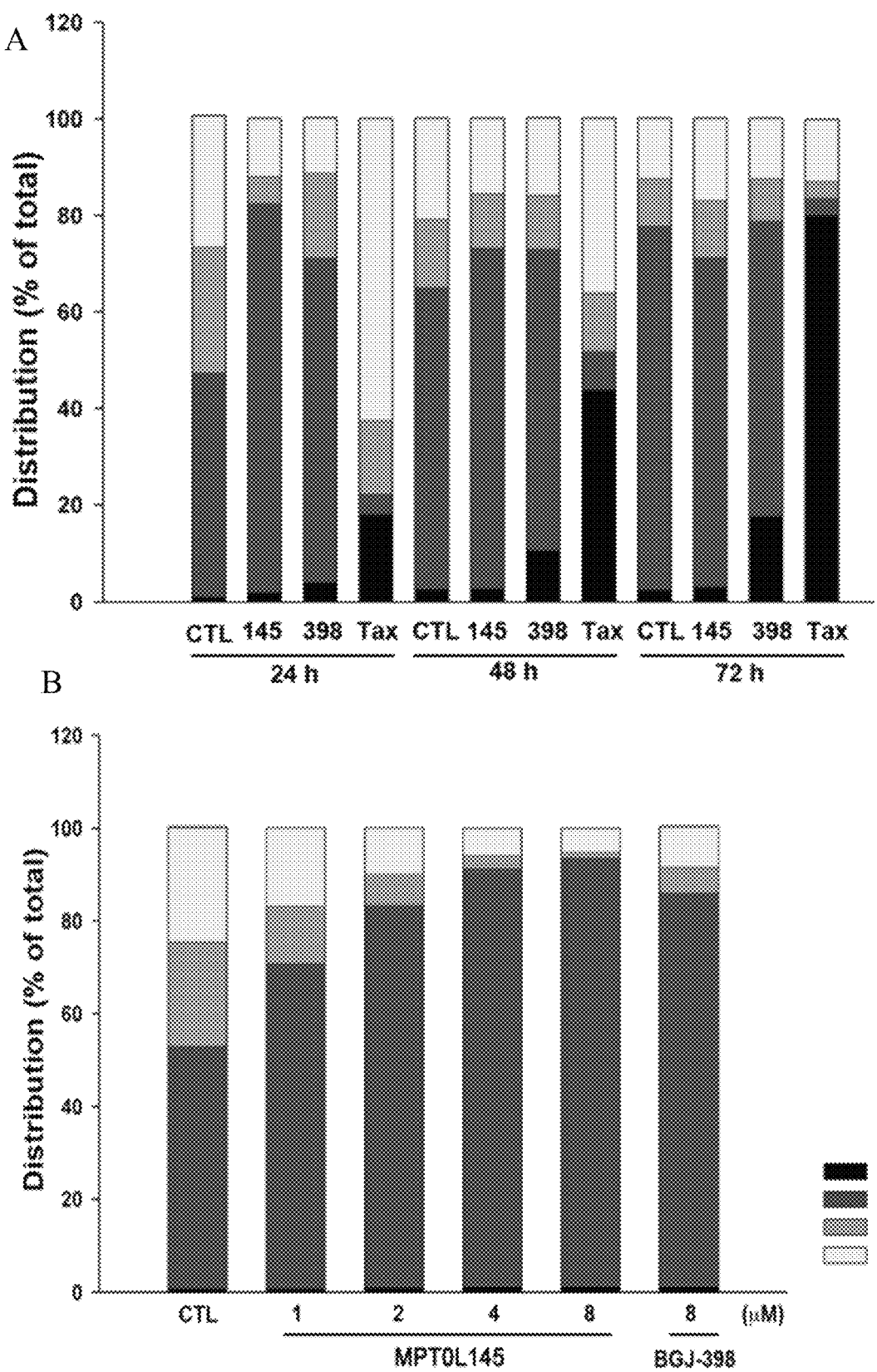
FIG. 3A to 3D show effects of MPT0L145 on cell cycle distribution. A. RT-112 cells were treated with MPT0L145 (4 μM), BGJ-398 (4 μM) and Paclitaxel (0.1 μM) for the indicated times, and cell cycle distribution was analyzed via flow cytometry. (CTL: control group, 145: MPT0L145, 398: BGJ-398, Tax: Paclitaxel) B. RT-112 cells were exposed to the indicated concentrations of MPT0L145 and BGJ-398 (8 μM) for 24 h and subjected to flow cytometry. C. Effects of MPT0L145 on cell cycle regulator proteins. RT-112 cells were treated with different concentrations of MPT0L145 for 24 h and subjected to western blot. D. RT-112 cells were treated with MPT0L145 and Paclitaxel for 72 h. Apoptosis was assessed via detection of cleaved caspase-3 and PARP.
Figure 3:
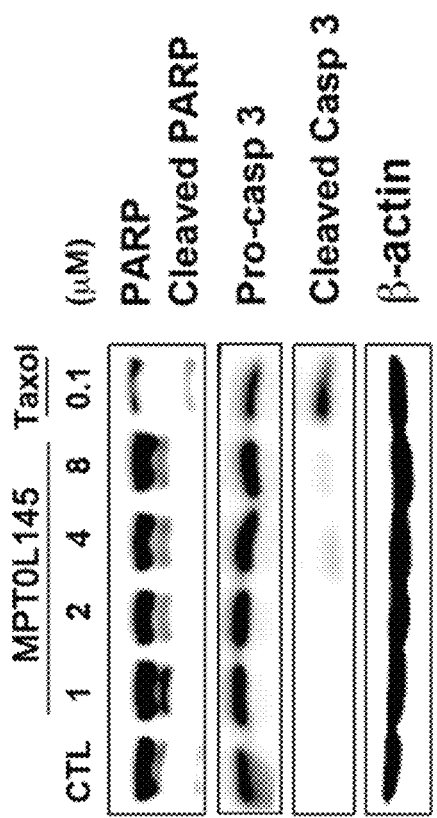
Figure 3:
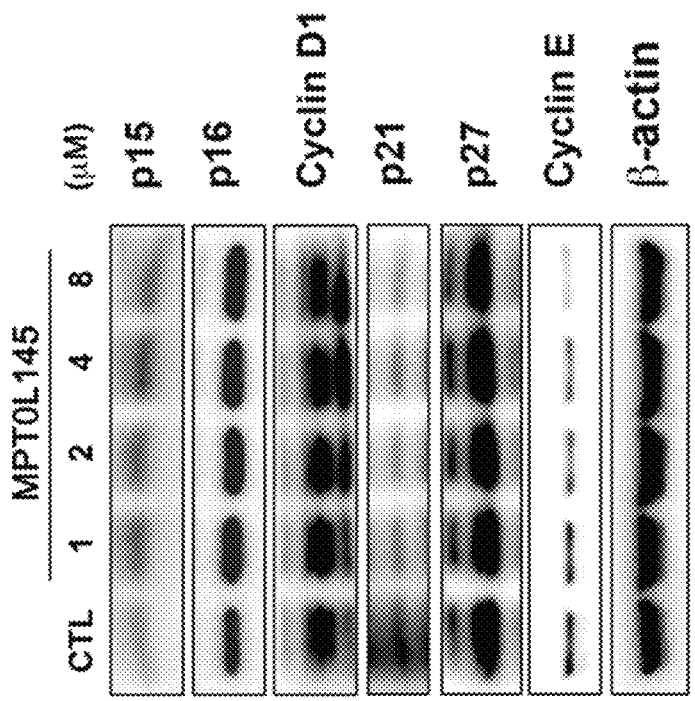

Example 43 MPT0L145 Induces Cell Cycle Arrest at the G0/G1 Phase in Bladder Cancer Cells We observed that genes associated with cell cycle progression were decreased in MPT0L145-treated cells. Accordingly, we further examined the effects of MPT0L145 on cell cycle progression in RT-112 cells. The data revealed that MPT0L145 induced G0/G1 cell cycle arrest to a dramatic extent in 24 h. This phenomenon was also observed in the cells treated with BGJ-398 (FIG. 3A). Interestingly, however, MPT0L145 did not promote accumulation of the sub-G1 phase, a marker of apoptotic cell death, in 72 h, whereas BGJ-398 and paclitaxel induced pronounced apoptosis at 48 h to 72 h. Moreover, the effect of MPT0L145 on G0/G1 arrest was concentration-dependent (FIG. 3B). These findings indicate that the anti-growth activity of MPT0L145 occurs, at least in part, through disrupting cell cycle progression at the G0/G1 phase. Next, we examined expression of G0/G1 regulatory proteins via western blot. Our data showed a slight increase in p16 and marked decrease in cyclin E levels (FIG. 3C). The possibility of MPT0L145-induced apoptosis was further eliminated by examining cleavage of caspase-3 and its substrate, PARP, in 72 h, compared with paclitaxel (FIG. 3D). The results collectively suggest that MPT0L145 exhibits anti-growth activity in bladder cancer cells, at least partly through inducing G0/G1 cell cycle arrest.

Example 44 Antitumor Activity of MPT0L145 in RT-112 Xenograft Model

To evaluate the anticancer activity of MPT0L145 in the preclinical setting, we examined its effects in athymic nude mice bearing established RT-112 tumor xenografts. Eight-week-old female athymic nude mice were group-housed in the TMU Laboratory Animal Center (Taipei, Taiwan) under conditions of constant photoperiod (12 h light/12 h dark at 21-0023° C. and 60-85% humidity) with ad libitum access to sterilized food and water. All animal experiments followed ethical standards, and protocols as previously described [50]. Each mouse was inoculated subcutaneously with $1\times10^6$ RT-112 cells in a total volume of 0.1 mL serum-free medium containing 50% Matrigel (BD Biosciences). As tumors became established (~100 mm3), mice were randomized to four groups (n=5) that received the following treatments: (a) 0.5% carboxymethyl cellulose/0.1% Tween 80 vehicle, (b) cisplatin at 5 mg/kg/wk, MPT0L145 at (c) 5 mg/kg/d or (d) 10 mg/kg/d by intraperitoneal injection (ip). Tumors were measured weekly using calipers. Tumor volume (mm3) was calculated from w2×½ (w=width, l=length in mm of the tumor).

MPT0L145 significantly suppressed tumor growth in a dose-dependent manner. The percentages of tumor growth inhibition (% TGI) of cisplatin (5 mg/kg) and MPT0L145 (5 and 10 mg/kg) are 56.3%, 61.4% and 74.6%, respectively. MPT0L145 exhibited not only comparable antitumor activity to cisplatin, but also better safety, as established from assessment of body weight loss after treatment. Accordingly, we conclude that MPT0L145 possesses significant antitumor activity in vivo.

| Compound | MPT0L145 | MPT0L145 | Cisplatin |
|---|---|---|---|
| Treatment | 5 mg/kg/d, i.p. | 10 mg/kg/d, i.p. | 5 mg/kg/wk, i.p. |
| Tumor growth inhibition (%) | 61.4 | 74.6 | 56.3 |
| Body weigh loss | No | No | Yes |

Example 45 In Vitro Inhibitory Effects of MPT0L145 on Protein Kinases and Lipid Kinase Kinase assays. For most assays, kinase-tagged T7 phage strains were prepared in an *E. coli* host derived from the BL21 strain. *E. coli* were grown to log-phase and infected with T7 phage and incubated with shaking at 32° C. until lysis. The lysates were centrifuged and filtered to remove cell debris. The remaining kinases were produced in HEK-293 cells and subsequently tagged with DNA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% BSA, 0.05% Tween 20, 1 mM DTT) to remove unbound ligand and to reduce non-specific binding. Binding reactions were assembled by combining kinases, liganded affinity beads, and test compounds in 1× binding buffer (20% SeaBlock, 0.17×PBS, 0.05% Tween 20, 6 mM DTT). All reactions were performed in polystyrene 96-well plates in a final volume of 0.135 ml. The assay plates were incubated at room temperature with shaking for 1 hour and the affinity beads were washed with wash buffer (1×PBS, 0.05% Tween 20). The beads were then re-suspended in elution buffer (1×PBS, 0.05% Tween 20, 0.5 μM non-biotinylated affinity ligand) and incubated at room temperature with shaking for 30 minutes. The kinase concentration in the eluates was measured by qPCR.

Compound Handling.

An 11-point 3-fold serial dilution of each test compound was prepared in 100% DMSO at 100× final test concentration and subsequently diluted to 1× in the assay (final DMSO concentration=1%). Most Kds were determined using a compound top concentration=30,000 nM. If the initial Kd determined was <0.5 nM (the lowest concentration tested), the measurement was repeated with a serial dilution starting at a lower top concentration. A Kd value reported as 40,000 nM indicates that the Kd was determined to be >30,000 nM.

Binding Constants (Kds).

Binding constants (Kds) were calculated with a standard dose-response curve using the Hill equation:

$$\text{Response} = \text{Background} + \frac{\text{Signal} - \text{Background}}{1 + (Kd^{Hill\,Slope} / Dose^{Hill\,Slope})}$$

The Hill Slope was set to −1. Curves were fitted using a non-linear least square fit with the Levenberg-Marquardt algorithm.

The results of in vitro inhibitory effects of MPT0L145 on protein kinases are shown in the table below.

| Kinase | $K_d$ (nM) |
|---|---|
| FGFR1 | 130 |
| FGFR3 | 270 |
| FGFR2 | 670 |
| FGFR4 | 7500 |
| CSF1R | 340 |
| TYK2 | 660 |
| PDGFRB | 680 |
| KIT | 950 |
| FLT3 | 1300 |
| VEGFR2 | 3100 |
| Erbb2 | 10000 |
| ACVR1B | >10000 |
| ADCK3 | >10000 |
| AKT1 | >10000 |
| AKT2 | >10000 |
| AURKB | >10000 |
| AXL | >10000 |
| BMPR2 | >10000 |
| BRAF | >10000 |
| BTK | >10000 |
| CDK3 | >10000 |
| CDK9 | >10000 |
| CSNK1D | >10000 |
| DCAMKL1 | >10000 |
| EGFR | >10000 |
| EPHA2 | >10000 |
| ERBB4 | >10000 |
| ERK1 | >10000 |
| FAK | >10000 |
| GSK3B | >10000 |
| IGF1R | >10000 |
| IKK-alpha | >10000 |
| IKK-beta | >10000 |
| INSR | >10000 |
| KIT | >10000 |
| LKB1 | >10000 |
| MAPKAPK2 | >10000 |
| MEK1 | >10000 |
| MEK2 | >10000 |
| MET | >10000 |
| MKNK1 | >10000 |
| MKNK2 | >10000 |
| MLK1 | >10000 |
| p38-alpha | >10000 |
| p38-beta | >10000 |
| PDGFRA | >10000 |
| PDPK1 | >10000 |
| PIK3CA | >10000 |
| PIK3CG | >10000 |
| PIM1 | >10000 |
| PIM2 | >10000 |
| PIM3 | >10000 |
| PLK1 | >10000 |
| PLK3 | >10000 |
| RAF1 | >10000 |
| RET | >10000 |
| ROCK2 | >10000 |
| SRPK3 | >10000 |
| TGFBR1 | >10000 |
| TSSK1B | >10000 |
| YANK3 | >10000 |
| ZAP70 | >10000 |

The results of in vitro inhibitory effects of MPT0L145 on lipid kinases are shown in the table below.

| Gene Symbol | Kd (nM) |
|---|---|
| PIK3C3 | 0.53 |
| PIK3C2B | 1000 |
| PIKFYVE | 2600 |
| PIK4CB | 6500 |
| PIP5K2B | >10000 |
| PIP5K2C | >10000 |
| PIK3C2G | >10000 |
| PIK3CA | >10000 |
| PIK3CB | >10000 |
| PIK3CD | >10000 |
| PIK3CG | >10000 |
| PIP5K1A | >10000 |
| PIP5K1C | >10000 |

Example 46 In Vitro Inhibitory Effects of MPT0L145 on Mutant FGFR3

FGFR aberrations are common in a wide variety of cancers, such as gene amplifications or activating mutations. The cancers most commonly affected were urothelial (32% FGFR-aberrant); breast (18%); endometrial (13%), squamous lung cancers (13%), and ovarian cancer (9%). In urothelial cancers, the majority of aberrations were activating mutations in FGFR3, including S249C, R248C, Y373C, G370C, and K650M (Clin Cancer Res. 2016 Jan. 1; 22(1): 259-67.). In multiple myeloma, active FGFR3 mutation (Y373C, and K650E) are reportedly important in tumor progression (Oncogene. 2001 Jun. 14; 20(27):3553-62.). The mutation of FGFR3 (V555M) is also identified as a mechanism of acquire resistance to FGFR inhibitors (Oncogene. 2013 Jun. 20; 32(25):3059-70.). Moreover, constitutive activating mutation of the FGFR3b (G697C) is found in oral squamous cell carcinomas (Int J Cancer. 2005 Oct. 20; 117(1):166-8.). Therefore, we examined the inhibitor activity of MPT0L145 on FGFR3 with active mutation. Compare to wild-type FGFR3, MPT0L145 showed comparable activity in inhibiting FGFR3 (G697C), and with better activity in specifically inhibiting FGFR3 (K650E). The data suggests that MPT0L145 can inhibit not only wild-type FGFR3, but also FGFR3 carrying active mutation (K650E, G697C).

The compound and assay method are similar to those mentioned in Example 45. The results of the In vitro inhibitory effects of MPT0L145 on mutant FGFR3 are shown in the table below.

| Gene Symbol | Kd (nM) |
|---|---|
| FGFR3 | 390 |
| FGFR3(G697C) | 390 |
| FGFR3(K650E) | 240 |
| FGFR3(V555M) | >10000 |

Example 47 Rational Combination of MPT0L145 and Agents Known to Induce Pro-Survival Autophagy in the Treatment of Cancer Autophagy is an important cellular recycling mechanism in which portions of cytosol or organelles are sequestered into a double-membrane structure and delivered to lysosome for degradation. Therefore, the rationale of targeting autophagy addiction in cancer was proposed by combining autophagy inhibition with agents that induce autophagy as a pro-survival response to increase their therapeutic efficacy. From our data, MPT0L145 is a potent inhibitor of PIK3C3, which is important in the progression of autophagy ($K_D$=0.53 nM). Therefore, we examined the combination of MPT0L145 with agents known to induce pro-survival autophagy. Our preliminary data suggested a synergistic interaction when MPT0L145 combined with Gefitinib in non-small cell lung cancer A549 cells, and Gemcitabine in pancreatic cancer Panc1 cells.

Figure 4:
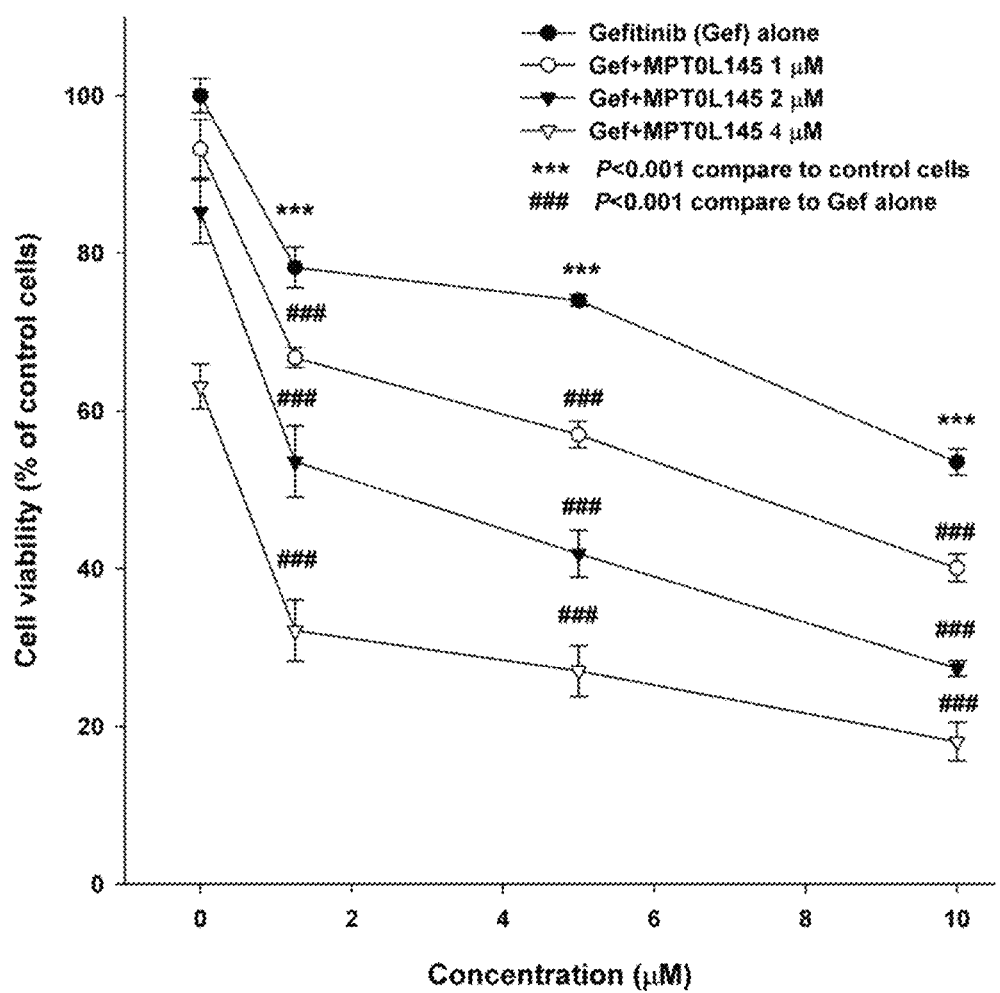
FIGS. 4A and 4B show the cell viability results (A) and CI values results (B) in A549 cells.
Figure 4:
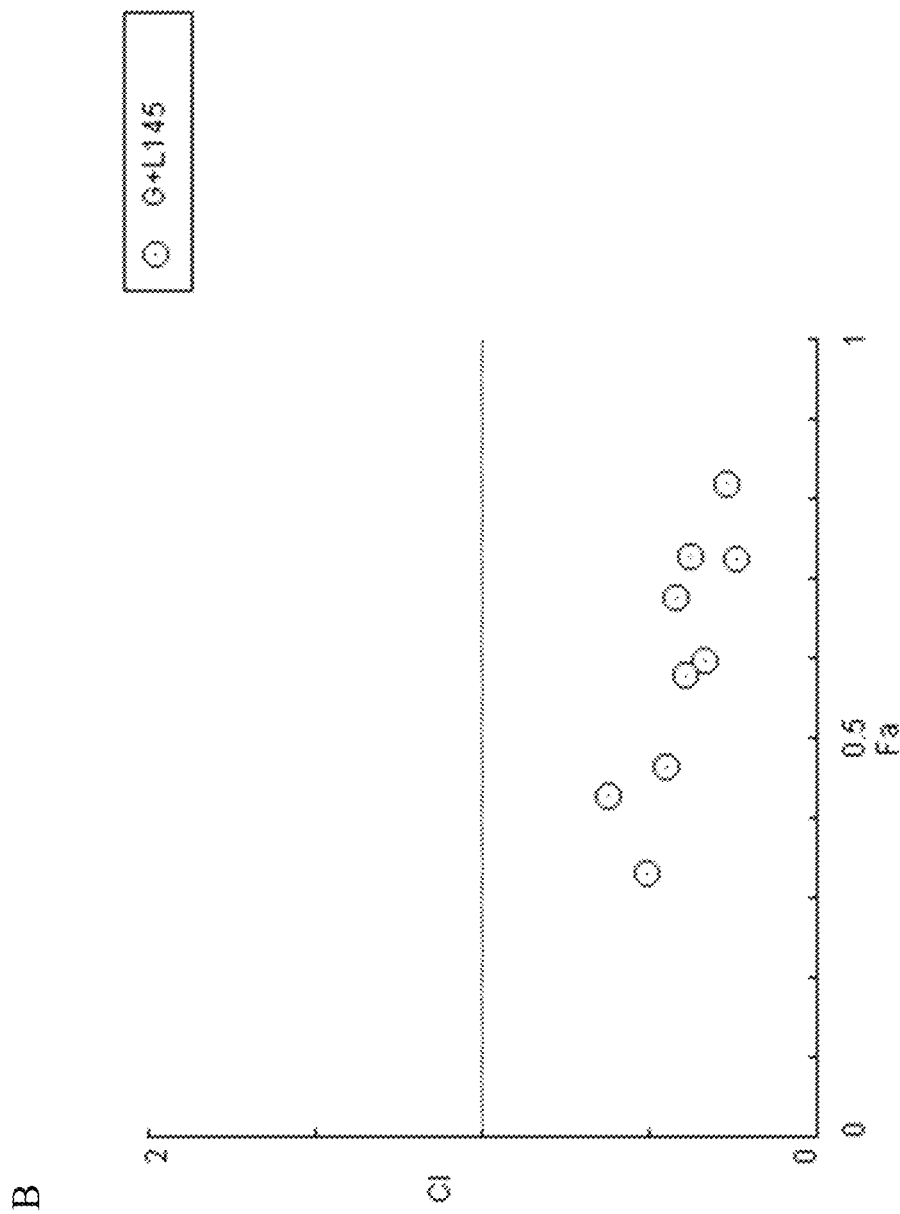

MTT assay was used in A549 cells or Panc1 cell (72 h). Cells were seeded in 96-well plates and exposed to DMSO, or indicated compounds for 72 hours. Cell viability was assessed using the 3-(4,5-dimethylthiazol-2-yl)-2,5-diphenyltetrazolium bromide (MTT) assay as described previously [46]. Briefly, 100 µl of 0.5 mg/ml MTT were added to each well and incubated at 37° C. for 1 hour. After that, 100 µl of extraction reagents (0.1 M sodium acetate buffer for suspension cells or DMSO for attached cells) were added to each well to lyse cells and absorbance at 550 nm was measured. Cell viability was expressed as the percentage of surviving cells in drug-treated versus DMSO-treated control cells (which was considered as 100% viability). The concentration that inhibits 50% of cell growth (IC50) were determined according to the dose-effect curves. The combination index (CI) value was determined from the fraction-affected value of each drug combination according to the Chou-Talalay method by using CompuSyn software (ComboSyn, Inc.), and a combination index value below 1 represents synergism (Pharmacol Rev. 2006 September; 58(3): 621-81.). The cell viability results and CI values results in A549 cells are shown in FIGS. 4A and 4B, respectively, and are also shown in the table below.

| Gefitinib (µM) | MPT0L145(µM) | Effect | CI |
|---|---|---|---|
| 1.25 | 1.0 | 0.333 | 0.51078 |
| 5.0 | 1.0 | 0.43 | 0.62487 |
| 10.0 | 1.0 | 0.599 | 0.34009 |
| 1.25 | 2.0 | 0.464 | 0.45105 |
| 5.0 | 2.0 | 0.581 | 0.39447 |
| 10.0 | 2.0 | 0.727 | 0.24181 |
| 1.25 | 4.0 | 0.678 | 0.42583 |
| 5.0 | 4.0 | 0.73 | 0.38142 |
| 10.0 | 4.0 | 0.819 | 0.27111 |

Figure 5:
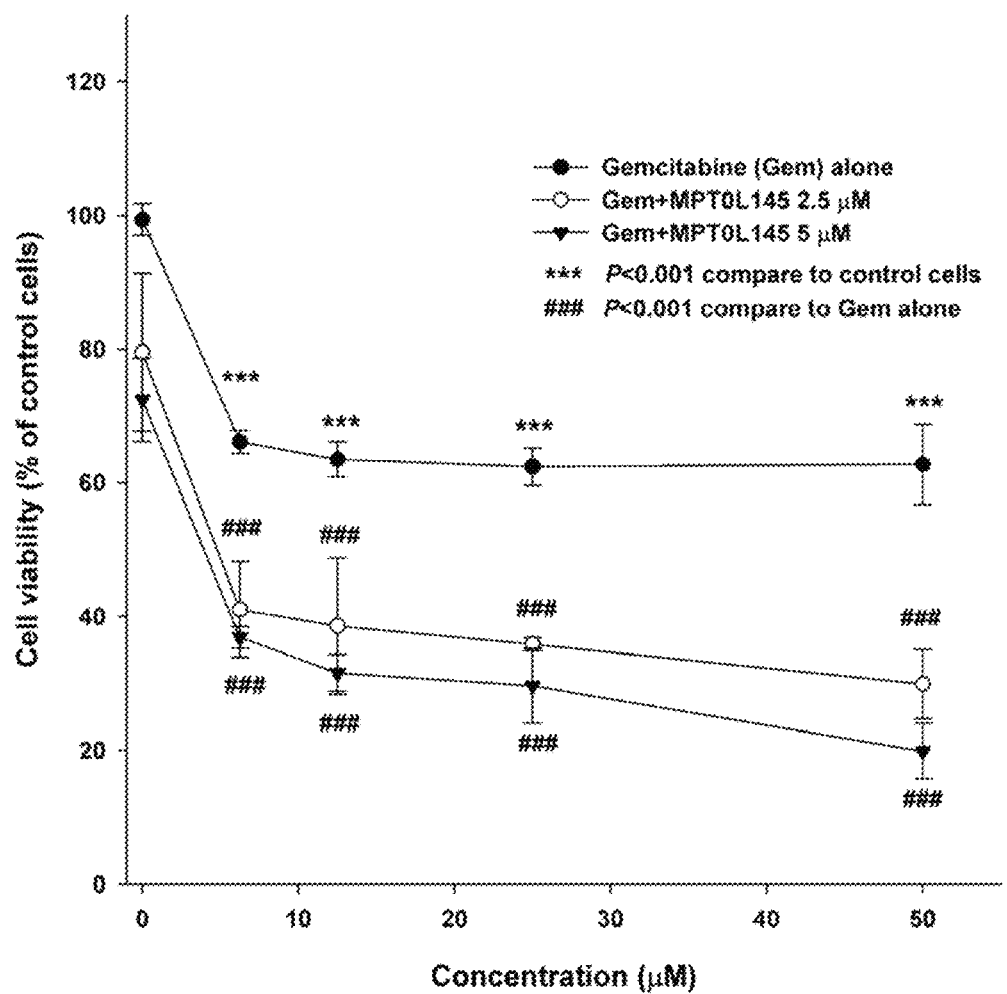
FIGS. 5A and 5B show the cell viability results (A) and CI values results (B) in Panc1 cells.
Figure 5:
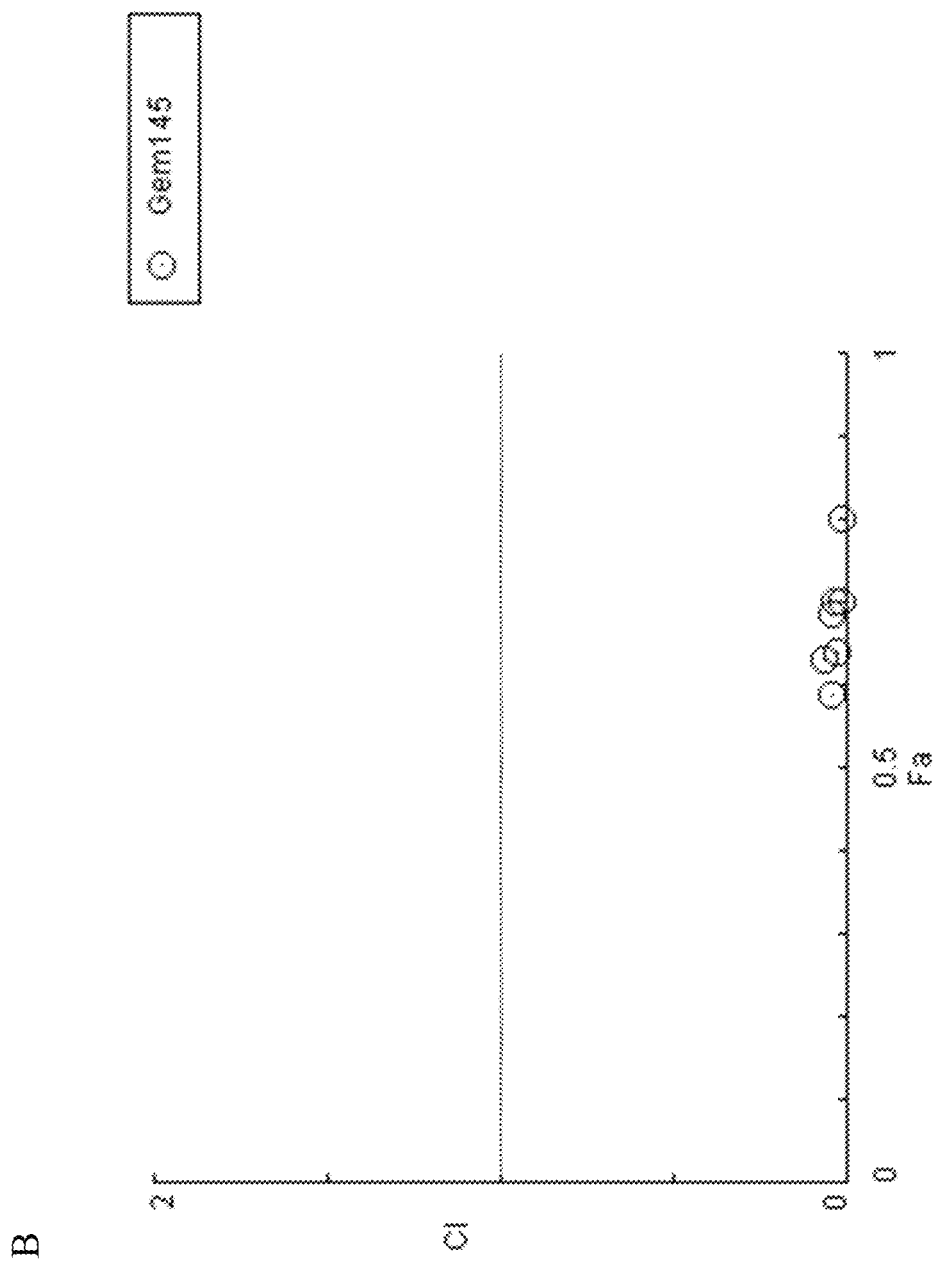

The cell viability results and CI values results in A549 cells are shown in FIGS. 5A and 5B, respectively, and are also shown in the table below.

| Gemcitabine (µM) | MPT0L145(µM) | Effect | CI |
|---|---|---|---|
| 6.25 | 2.5 | 0.59 | 0.0492 |
| 12.5 | 2.5 | 0.641 | 0.03376 |
| 25 | 2.5 | 0.642 | 0.0335 |
| 50 | 2.5 | 0.701 | 0.02099 |
| 6.25 | 5 | 0.632 | 0.07226 |
| 12.5 | 5 | 0.685 | 0.04786 |
| 25 | 5 | 0.703 | 0.04128 |
| 50 | 5 | 0.801 | 0.01634 |

We claim:

1. A compounds having the following Formula (I):

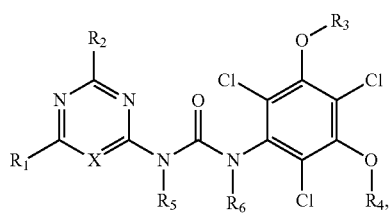

(I)

wherein

X is C, N, O or S;

R1 is cycloalkyl; aryl unsubstituted or substituted by halo, hydroxy, amino, nitro, cyano, alkyl, alkenyl, alkynyl, alkoxy, alkylthio, alkoxyalkyl, alkylamino, or heteroaryl having 1 to 3 heteroatoms selected from the group consisting of N, O and S; heteroalkyl unsubstituted or substituted by halo, hydroxy, amino, nitro, cyano, alkoxy, alkylthio, alkoxyalkyl, alkylamino, heteroaryl having 1 to 3 heteroatoms selected from the group consisting of N, O and S; or NR7R8 wherein R7 is selected from the group consisting of H, nitro, amino, cyano, alkyl, alkenyl, alkynyl, aryl, heteroaryl or C1-10alkylpiperazinylcarbonylphenyl wherein alkyl, alkenyl, alkynyl, aryl and heteroaryl are each independently substituted by heteroaryl having 1 to 3 heteroatom selected from the group consisting of N, O and S and substituted by alkyl, alkenyl or alkynyl or alkoxy; R8 is selected from the group consisting of H, nitro, amino, cyano, alkyl, alkenyl, alkynyl, aryl or heteroaryl wherein alkyl, alkenyl, alkynyl, aryl and heteroaryl are each independently substituted by heteroaryl having 1 to 3 heteroatom selected from the group consisting of N, O and S and substituted by alkyl, alkenyl or alkynyl or alkoxy;

R2 is H, halo, hydroxy, amino, nitro, cyano, alkyl, alkenyl, alkynyl or aryl unsubstituted or substituted by halo, hydroxy, amino, nitro, cyano, alkyl, alkenyl or alkynyl; and R3 and R4 are each independently selected from the group consisting of alkyl, alkenyl, alkynyl, alkoxy, alkylthio, alkoxyalkyl or alkylamino; and R5 and R6 are each independently selected from H, halo, hydroxy, amino, nitro, cyano, alkyl, alkenyl, alkynyl;

wherein the above-mentioned heteroaryl is unsubstituted or substituted by halo, hydroxy, amino, nitro, cyano, alkyl, alkenyl, alkynyl, alkoxy, alkylthio, alkoxyalkyl, alkylamino or aryl;

or a tautomer or stereoisomer thereof, or a pharmaceutically acceptable salt thereof.

2. The compound of claim 1, wherein halo is F, Cl or Br; alkyl is C1-10alkyl; alkenyl is C2-10alkenyl; alkynyl is C2-10alkynyl; alkoxy is C1-10alkoxy; aryl is 5- or 6-membered aryl; and heteroaryl is 5- or 6-membered heteroaryl and has 1 to 3 heteroatoms selected from the group consisting of N, O and S.

3. The compound of claim 1, wherein X is C; R1 is phenyl unsubstituted or substituted by halo, cyano, nitro, C1-10alkoxy or C5-12heteroaryl having 1 to 3 heteroatoms selected from the group consisting of N, O and S and unsubstituted or substituted by C1-10alkyl; or unsubstituted or substituted heteroaryl having 1 to 3 heteroatoms selected from the group consisting of N, O and S; R2 is H; R3 and R4 are each independently C1-10alkyl; and R5 and R6 are each independently H or C1-10alkyl.

4. The compound of claim 1, wherein X is C; R1 is phenyl, C1-10alkylpiperazinylphenyl, C1-10alkyloxyphenyl, halophenyl, cyanophenyl, nitrophenyl, furyl or pyridinyl.

5. The compound of claim 1, wherein X is C; R1 is phenyl, (4-ethylpiperazinyl-1-yl)phenyl, phenyl, 4-methoxyphenyl, 4-fluorophenyl, 4-chlorophenyl, 4-cyanophenyl, nitrophenyl, 2-furyl, 3-pyridinyl or 4-pyridinyl; R2 is H; R3 and R4 are each independently CH3; and R5 and R6 are each independently H or C1-10alkyl.

6. The compound of claim 1, wherein X is C or N; R1 is NR7R8 wherein R7 and R8 are each independently selected from the group consisting of H, C1-10alkyl substituted by 6-membered heteroaryl unsubstituted or substituted by C1-10alkyl; phenyl substituted by 6-membered heteroaryl having 1 to 3 heteroatoms selected from the group consisting of N, O and S and substituted by C1-10alkyl; R2 is H, halo or phenyl; R3 and R4 are each independently C1-10alkyl; and R5 and R6 are each independently H or C1-10alkyl.

7. The compound of claim 1, wherein X is C or N; R1 is NR7R8 wherein R7 is C1-10alkylpiperazinylphenyl, piperidinylC1-10alkyl, C1-10alkylpiperazinylC1-10alkyl or C1-10alkylpiperazinylcarbonylphenyl and R8 is H; R2 is H, halo or phenyl; R3 and R4 are each independently C1-10alkyl; and R5 and R6 are each independently H or C1-10alkyl.

8. The compound of claim 1, wherein X is C or N; R1 is NR7R8 wherein R7 is ethylpiperazinylphenyl, methylpiperazinylethyl or ethylpiperazinylcarbonylphenyl and R8 is H; R2 is H, phenyl or Cl; R3 and R4 are each independently C1-10alkyl; and R5 and R6 are each independently H or C1-10alkyl.

9. The compound of claim 1, which is selected from the group consisting of:
1-(6-((4-(4-ethylpiperazin-1-yl)phenyl)amino)pyrimidin-4-yl)-1-methyl-3-(2,4,6-trichloro-3, 5-dimethoxyphenyl)urea;
1-(6-((4-(4-ethylpiperazin-1-yl)phenyl)amino)-2-phenylpyrimidin-4-yl)-1-methyl-3-(2,4,6-trichloro-3,5-dimethoxyphenyl)urea;
1-(4-((4-(4-ethylpiperazin-1-yl)phenyl)amino)-1,3,5-triazin-2-yl)-1-methyl-3-(2,4,6-trichloro-3,5-dimethoxyphenyl)urea;
1-(4-chloro-6-((4-(4-ethylpiperazin-1-yl)phenyl)amino)-1,3,5-triazin-2-yl)-1-methyl-3-(2,4,6-trichloro-3,5-dimethoxyphenyl)urea;
1-methyl-1-(6-((2-(piperidin-1-yl)ethyl)amino)pyrimidin-4-yl)-3-(2,4,6-trichloro-3, 5-dimethoxyphenyl)urea;
1-methyl-1-(6-((2-(4-methylpiperazin-1-yl)ethyl)amino)pyrimidin-4-yl)-3-(2,4,6-trichloro-3, 5-dimethoxyphenyl)urea;
1-(6-((4-(4-ethylpiperazine-1-carbonyl)phenyl)amino)pyrimidin-4-yl)-1-methyl-3-(2,4,6-trichloro-3,5-dimethoxyphenyl)urea;
1-(6-(4-(4-ethylpiperazin-1-yl)phenyl)pyrimidin-4-yl)-1-methyl-3-(2,4,6-trichloro-3, 5-dimethoxyphenyl)urea;
1-methyl-1-(6-phenylpyrimidin-4-yl)-3-(2,4,6-trichloro-3, 5-dimethoxyphenyl)urea;
1-(6-(4-methoxyphenyl)pyrimidin-4-yl)-1-methyl-3-(2,4,6-trichloro-3,5-dimethoxyphenyl)urea;
1-(6-(4-fluorophenyl)pyrimidin-4-yl)-1-methyl-3-(2,4,6-trichloro-3, 5-dimethoxyphenyl)urea;
1-(6-(4-chlorophenyl)pyrimidin-4-yl)-1-methyl-3-(2,4,6-trichloro-3,5-dimethoxyphenyl)urea;
1-(6-(4-cyanophenyl)pyrimidin-4-yl)-1-methyl-3-(2,4,6-trichloro-3, 5-dimethoxyphenyl)urea;
1-(6-(3-cyanophenyl)pyrimidin-4-yl)-1-methyl-3-(2,4,6-trichloro-3, 5-dimethoxyphenyl)urea;
1-methyl-1-(6-(3-nitrophenyl)pyrimidin-4-yl)-3-(2,4,6-trichloro-3, 5-dimethoxyphenyl)urea;
1-(6-(furan-2-yl)pyrimidin-4-yl)-1-methyl-3-(2,4,6-trichloro-3,5-dimethoxyphenyl)urea;
1-methyl-1-(6-(pyridin-3-yl)pyrimidin-4-yl)-3-(2,4,6-trichloro-3,5-dimethoxyphenyl)urea; and
1-methyl-1-(6-(pyridin-4-yl)pyrimidin-4-yl)-3-(2,4,6-trichloro-3,5-dimethoxyphenyl)urea;
or a tautomer or stereoisomer thereof, or a pharmaceutically acceptable salt thereof.

10. The compound 1-(4-((4-(4-ethylpiperazin-1-yl)phenyl)amino)-1,3,5-triazin-2-yl)-1-methyl-3-(2,4,6-trichloro-3,5-dimethoxyphenyl)urea, having the following formula:

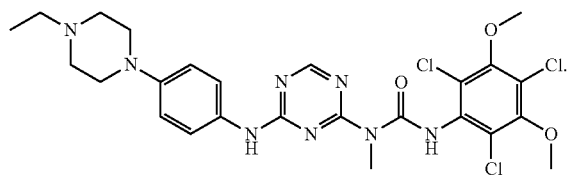 [SMILES: CCN1CCN(c2ccc(Nc3ncnc(N(C)C(=O)Nc4c(Cl)c(OC)c(Cl)c(OC)c4Cl)n3)cc2)CC1]

11. A pharmaceutical composition, comprising a compound of claim 1 and a pharmaceutically acceptable carrier.

12. The pharmaceutical composition of claim 11, which further comprises one or more second therapeutic agents.

13. The pharmaceutical composition of claim 12, wherein the second therapeutic agent is a mitotic inhibitor; an anthracycline antibiotic; a nucleoside analog; an EGFR inhibitor; an folate antimetabolite; cisplatin and carboplatin.

14. The pharmaceutical composition of claim 12, wherein the second therapeutic agent is tamoxifen, taxol, vinblastine, etoposide (VP-16), adriamycin, 5-fluorouracil (5FU), camptothecin, actinomycin-D, mitomycin C, combretastatin(s), more particularly docetaxel (taxotere), cisplatin (CDDP), cyclophosphamide, doxorubicin, methotrexate, paclitaxel, vincristine, gefitinib, or erlotinib.

15. A method of treating cancer selected from the group consisting of: neuroblastoma; lung cancer; bile duct cancer; non-small cell lung carcinoma; hepatocellular carcinoma; head and neck squamous cell carcinoma; squamous cell cervical carcinoma; lymphoma; nasopharyngeal carcinoma; gastric cancer; colon cancer; uterine cervical carcinoma; gall bladder cancer; prostate cancer; breast cancer; testicular germ cell tumors; colorectal cancer; glioma; thyroid cancer; basal cell carcinoma; gastrointestinal stromal cancer; hepatoblastoma; endometrial cancer; ovarian cancer; pancreatic cancer; renal cell cancer, Kaposi's sarcoma, chronic leukemia, sarcoma, rectal cancer, throat cancer, melanoma, colon cancer, bladder cancer, mastocytoma, mammary carcinoma, mammary adenocarcinoma, pharyngeal squamous cell carcinoma, testicular cancer, gastrointestinal cancer, or stomach cancer and urothelial cancer, comprising administering to the subject an effective amount of the compound of claim 1.

16. The method of claim 15, wherein the cancer is bladder cancer, liver cancer, gastric cancer, myeloma, sarcoma, colorectal cancer, lung cancer, breast cancer or hepatocellular carcinoma.

17. The method of claim 15, wherein the cancer is a FGFR-activated cancer.

* * * * *